(12) United States Patent
Sheva et al.

(10) Patent No.: US 12,385,054 B2
(45) Date of Patent: Aug. 12, 2025

(54) REMOVAL OF CONSTRUCTS FROM TRANSFORMED CELLS

(71) Applicant: Protalix Ltd., Carmiel (IL)

(72) Inventors: Maor Sheva, Kfar-Vradim (IL); Uri Hanania, Carmiel (IL)

(73) Assignee: Protalix Ltd., Carmiel (IL)

( * ) Notice: Subject to any disclaimer, the term of this patent is extended or adjusted under 35 U.S.C. 154(b) by 95 days.

(21) Appl. No.: 17/777,669

(22) PCT Filed: Nov. 19, 2019

(86) PCT No.: PCT/IL2019/051266
§ 371 (c)(1),
(2) Date: May 18, 2022

(87) PCT Pub. No.: WO2021/100034
PCT Pub. Date: May 27, 2021

(65) Prior Publication Data
US 2023/0022576 A1    Jan. 26, 2023

(51) Int. Cl.
*C12N 15/82* (2006.01)
*C12N 9/22* (2006.01)
*C12N 15/11* (2006.01)

(52) U.S. Cl.
CPC .......... *C12N 15/8222* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 2003/0154518 A1 | 8/2003 | Signer et al. | |
| 2015/0024500 A1* | 1/2015 | Yu | C12N 15/102 435/325 |
| 2019/0055583 A1* | 2/2019 | Shalek | C12Q 1/68 |
| 2019/0071717 A1* | 3/2019 | Zhang | C12N 15/113 |
| 2021/0032622 A1* | 2/2021 | Police | C12N 15/111 |

FOREIGN PATENT DOCUMENTS

| | | | | |
|---|---|---|---|---|
| JP | 2019-521717 | 8/2019 | | |
| WO | WO-2015089351 A1 * | 6/2015 | ......... | A01K 67/0276 |
| WO | WO 2018/022747 | 2/2018 | | |
| WO | WO-2018022747 A1 * | 2/2018 | .......... | C12N 15/113 |
| WO | WO 2019/092505 | 5/2019 | | |
| WO | WO 2021/100034 | 5/2021 | | |

OTHER PUBLICATIONS

Aubrey, Brandon J., et al. "An inducible lentiviral guide RNA platform enables the identification of tumor-essential genes and tumor-promoting mutations in vivo." Cell reports 10.8 (2015): 1422-1432 (Year: 2015).*
International Preliminary Report on Patentability Dated Jun. 2, 2022 From the International Bureau of WIPO Re. Application No. PCT/IL2019/051266. (7 Pages).
International Search Report and the Written Opinion Dated Jul. 21, 2020 From the International Searching Authority Re. Application No. PCT/IL2019/051266. (12 Pages).
Aysha et al. "Synthetic Promoters: Designing the Cis Regulatory Modules for Controlled Gene Expression", Molecular Biotechnology, XP036547751, 60(8): 608-620, Published Online May 31, 2018.
Gao et al. "An Effective Strategy for Reliably Isolating Heritable and Cas9—Free *Arabidopsis* Mutants Generated by CRISPR/Cas9-Mediated Genome Editing", Plant Physiology, XP055548318, 171(3): 1794-1800, Published Online May 15, 2016.
Hanania et al. "Establishment of a Tobacco BY2 Cell Line Devoid of Plant-Specific Xylose and Fucose as a Platform for the Production of Biotherapeutic Proteins", Plant Biotechnology Journal, 15(9): 1120-1129, Published Online Mar. 3, 2017.
He et al. "Programmed Self-Elimination of CRISPR/Cas9 Construct Greatly Accelerates the Isolates of Edited and Transgene-Free Rice Plants", Molecular Plant, XP055654615, 11(9): 1210-1213, Published Online May 29, 2018.
Yau et al. "Less Is More: Strategies to Remove Marker Genes From Transgenic Plants", BMC Biotechnology, 18(36): 1-23, Published Online Apr. 23, 2013.
Notice of Reason(s) for Rejection Dated Sep. 26, 2023 From the Japan Patent Office Re. Application No. 2022-529327 and Its Translation Into English. (9 Pages).
Notice of Reason(s) for Rejection Dated Mar. 5, 2024 From the Japan Patent Office Re. Application No. 2022-529327 and Its Translation Into English. (8 Pages).

* cited by examiner

*Primary Examiner* — Weihua Fan

(57) ABSTRACT

A nucleic acid construct is disclosed which is removable after transformation. Methods of using same are disclosed as well.

8 Claims, 12 Drawing Sheets
Specification includes a Sequence Listing.

FIG. 12

| # | Name | Targeted sequence | Targeted genes |
|---|------|-------------------|----------------|
| 1 | crRNA1 | 5' GAGAAATTGGAGTCGGTTATTGG 3' | BY2-XylT-A<br>BY2-XylT-B |
| 2 | crRNA2 | 5' GATCGGAATTTGGAAACTGGG 3' | BY2-FucT-A<br>BY2-FucT-B<br>BY2-FucT-C |
| 3 | crRNA3 | 5' GCTGGCACGGCTAGCGTGCTTCGG 3' | BY2-FucT-A<br>BY2-FucT-B<br>BY2-FucT-C |
| 4 | crRNA4 | 5' GCCGCTTTCATTTCTAATTGTGG 3' | BY2-FucT-D<br>BY2-FucT-E |
| 5 | crRNA5 | 5' GGGCTTCTAAAGCTTGCAAGAGG 3' | BY2-FucT-D<br>BY2-FucT-E |

REMOVAL OF CONSTRUCTS FROM TRANSFORMED CELLS

RELATED APPLICATION

This application is a National Phase of PCT Patent Application No. PCT/IL2019/051266 having International filing date of Nov. 19, 2019. The contents of the above application are all incorporated by reference as if fully set forth herein in its entirety.

SEQUENCE LISTING STATEMENT

The ASCII file, entitled 92656SequenceListing.txt, created on May 18, 2022, comprising 25,025 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to a method of removing a construct used to transform cells and, more particularly, but not exclusively, to plant cells.

The CRISPR-Cas9, Cas12a (also known as Cpf1) and, recently discovered, CasX have proven to be highly efficient valuable tools for precise genome editing across a wide range of cell types and organisms. The CRISPR-Cas system is becoming an increasingly important tool for a wide range of targeted mutagenesis, gene replacement and other novel applications. However, such approaches might result in a transgenic cell line that harbors a long list of various transgenes, some of which are no longer required once they have accomplished their task.

In order to intervene in the glycosylation machinery and to humanize plant produced recombinant biotherapeutics, the CRISPR system was used to engineer the genome of BY-2 host cells and *N. Benthamiana* host plants (Hanania et al., 2017; Jansing et al., 2019; Mercx et al., 2017). The presence of selectable markers and nuclease genes (e.g. CRISPR-Cas9) that were used for the targeted mutations, not only may pose excessive metabolic burden on the cell's machinery, but may also limit their further application in subsequent transformations. Therefore, the removal of these genes is highly desirable.

To date, many approaches have been developed in whole plants, which segregate sexually, to eliminate the selectable marker that has been stably integrated into the plant genome. These methods include: (1) repeated back crosses and segregation; (2) Co-transformation using two constructs, one of which contains the selectable marker while the other harbors the desired gene of interest, thus allowing for subsequent removal of the selectable gene by genetic segregation; (3) Homologous recombination between direct repeats using the Cre recombinase microbial enzyme (Dale and Ow, 1991; Wang et al., 2005) or using the yeast FLP and R recombinases (Hare and Chua, 2002) and (4) transposable element-based systems (Yoder and Goldsbrough, 1994).

Additional approaches to avoid Cas9 integration within the plant genome include the following: (1) Transient expression of Cas9 (Chen et al., 2018; Zhang et al., 2016); (2) Transfection of preassembled complexes of purified Cas9 protein and guide RNA (RNP) into plant protoplasts (Woo et al., 2015); (3) Using 'suicide' transgenes, such as the BARNASE gene under the control of the rice REG2 promoter, that effectively kill all of the CRISPR-Cas9 containing pollen and embryos, assuring that any viable embryos will be free of foreign DNA (He et al., 2018) or (4) Coupling the CRISPR construct with an RNA interference element, which targets an herbicide resistance enzyme in rice (Lu et al., 2017), resulting in transgene-free mutated plants.

Unfortunately, besides being highly laborious and time consuming, most of these approaches are not applicable to cells in suspension, due to the asexual nature of propagation of these cells.

Previous experiments showed procedures for large chromosomal excision in a non-plant species (Hao et al., 2016; He et al., 2014; Xiao et al., 2013; Zhang et al., 2015) and large chromosomal excision in plant species (Cai et al., 2018; Li et al., 2019; Ordon et al., 2017; Zhou et al., 2014).

Additional background art includes US Patent Application No. 20030154518 and Yau et al BMC Biotechnol. 2013; 13: 36.

SUMMARY OF THE INVENTION

According to an aspect of the present invention, there is provided a nucleic acid construct comprising a nucleic acid sequence which encodes:
  (i) at least one nucleic acid agent operatively linked to a first promoter, wherein said agent is for editing or regulating at least one nucleic acid target of interest in an organism or cell of said organism;
  (ii) at least one construct-eliminating gRNA;
  (iii) a CRISPR endonuclease, wherein either said construct-eliminating gRNA or said CRISPR endonuclease is operatively linked to a second promoter, wherein said first promoter and said second promoter are selected such that initiation of transcription from said second promoter occurs following initiation of transcription from said first promoter in said organism or said cell of said organism; and
  (iv) at least two copies of a target sequence for said construct-eliminating gRNA.

According to another aspect of the present invention, there is provided an organism or a cell thereof comprising the nucleic acid constructs disclosed herein.

According to another aspect of the present invention, there is provided a plant or a plant cell comprising the nucleic acid construct disclosed herein.

According to another aspect of the present invention, there is provided a method of editing or regulating a nucleic acid target of interest in an organism or cell thereof comprising:
  (a) transforming the organism or isolated cells thereof with the nucleic acid construct described herein under conditions that promote editing or regulating of said nucleic acid of interest, wherein said conditions do not promote expression from said second promoter, and subsequently
  (b) culturing said organism or isolated cells thereof under conditions so as to promote expression from said second promoter, thereby editing or regulating the nucleic acid target of interest.

According to an embodiment, the first promoter is a constitutive promoter.

According to another embodiment, the second promoter is an inducible promoter.

According to another embodiment, the second promoter is a tissue-specific promoters or a developmental stage-specific promoter.

According to another embodiment, the first promoter is stronger than said second promoter.

According to another embodiment, the nucleic acid agent comprises a nucleic acid editing agent.

According to another embodiment, the nucleic acid editing agent is selected from the group consisting of CRISPR, TALEN, meganuclease and zinc finger nuclease.

According to another embodiment, when said at least one nucleic acid agent comprises a gRNA, said CRISPR endonuclease is operatively linked to said first promoter and said construct-eliminating gRNA is operatively linked to said second promoter.

According to another embodiment, the nucleic construct further encodes:

(v) a negative selectable marker.

According to another embodiment, the nucleic acid construct further encodes:

(vi) a positive selectable marker.

According to another embodiment, a first of said at least two copies is positioned 3' to (i), (ii) and (iii) and a second of said at least two copies is positioned 5' to (i), (ii) and (iii).

According to another embodiment, a first of said at least two copies is positioned 3' to (i), (ii), (iii), (v) and (vi), and a second of said at least two copies is positioned 5' to (i), (ii), (iii), (v) and (vi).

According to another embodiment, the negative selectable marker comprises CodA.

According to another embodiment, the inducible promoter is a heat inducible promoter.

According to another embodiment, the organism is a plant.

According to another embodiment, the plant comprises a *Nicotiana tabacum* plant.

According to another embodiment, the at least two copies of a target sequence for said gRNA comprises at least six copies of said target sequence for said gRNA, wherein three of said at least six copies are positioned 3' to (i), (ii) and (iii) and another three of said at least six copies are positioned 5' to (i), (ii) and (iii).

According to another embodiment, the nucleic acid target of interest is comprised in a gene.

According to another embodiment, the gene encodes a glycosylating enzyme.

According to another embodiment, the glycosylating enzyme comprises xylosyltransferase and/or fucosyltransferase.

According to another embodiment, the plant is a *Nicotiana tabacum* plant.

According to another embodiment, the plant cell is a BY-2 cell line.

According to another embodiment, the plant or plant cell is cultured as a suspension.

According to another embodiment, the organism or cell thereof or the plant or cell thereof is genetically modified to express a protein of interest.

According to another embodiment, the organism is a plant.

According to another embodiment, the step (a) is effected for at least 1 day.

According to another embodiment, the transforming is stably transforming.

According to another embodiment, the organism is a plant.

According to another embodiment, the step (a) is effected for at least one week.

According to another embodiment, the step (b) is effected for at least one week.

According to another embodiment, the cells are cultured as a suspension.

According to another embodiment, the cells are plant cells.

According to another embodiment, the nucleic acid of interest is a gene of interest.

According to another embodiment, the regulating comprises down-regulating said gene of interest.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

LB—left border, ZZZ—three repeats of 23 nucleotides each used as targets for gRNA-Z; NosP—Nopaline synthase promoter, HptH—Hygromycin phosphotransferase II; NosT-Nopaline synthase terminator, 35sP-35S cauliflower mosaic virus promoter with omega enhancer, hCas9-human-optimized Cas9 with the SV40 nuclear localization signal; OcST—Octopinesynthase terminator; codA—Cytosine deaminase (negative selectable marker); HSP—heat shock promoter (HSP 18.2) from *Arabidopsis thaliana*; U6—*Arabidopsis* U6 promoter, sgRNA-Z—Chimera of crRNA directed to the Z sequences at the boundaries of the vector with tracrRNA and terminator (5 repeats of T); sgRNA1-5, chimeras of the various crRNAs with tracrRNA, represent the five different crRNAs that were used to knock out FucT and XylT genes (Hanania et al., 2017); RB-right border.

Figure 2:
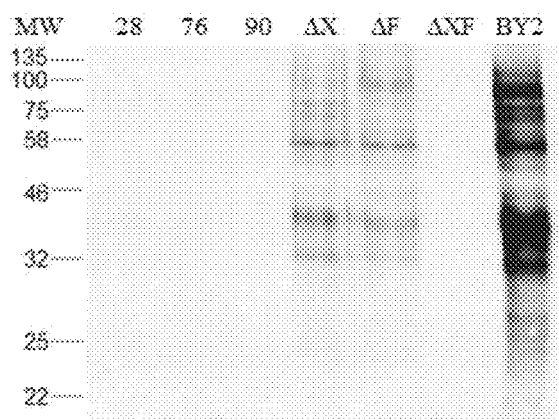

FIG. 2. Western blot using anti-HRP antibodies. Total protein was extracted from the 3 putative knockout cell lines 28, 76, 90, the non-transgenic BY-2 cells and three controls knockout cell lines. A total of 10 µg protein from each sample were loaded on 12% SDS-PAGE followed by Western blot using anti-HRP antibodies. ΔX, ΔF, ΔXF are the knockout cell lines established previously (Hanania et al. 2017) and used as controls: ΔX lacks glycans containing Xylose, ΔF lacks glycans containing Fucose, ΔXF lacks glycans containing both Xylose & Fucose respectively; MW—molecular weight marker in kDa.

Figure 3:
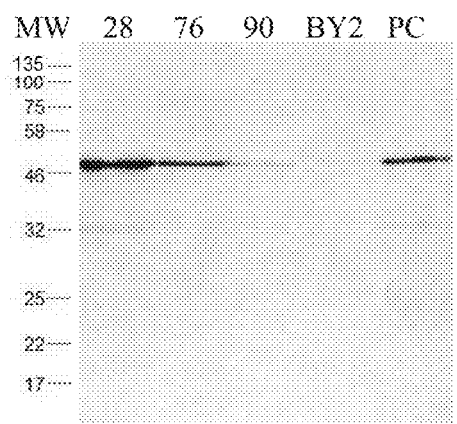

FIG. 3. Western blot using anti-codA antibodies. Total protein was extracted from the 3 knockout cell lines 28, 76, 90 and two control cell lines. A total of 10 µg protein from each sample were loaded on SDS-PAGE followed by Western blot using anti-codA antibodies. PC—positive control (cell line expressing codA); BY-2—negative control (the non-transgenic BY-2 cells); MW—molecular weight marker in kDa. Expected size of codA is ~49 kDa.

Figure 4:
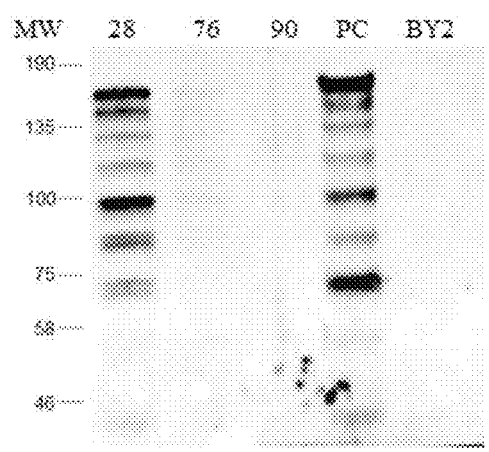

FIG. 4: Western blot using anti-Cas9 antibodies. Total protein was extracted from the 3 XylT/FucT knockout cell lines 28, 76, 90 and two control cell lines. A total of 10 µg protein from each sample were loaded on SDS-PAGE followed by Western blot using anti-Cas9 antibodies. PC—positive control (cell line expressing Cas9); BY-2—negative control (the non-transgenic BY-2 cells). MW—molecular weight marker in kDa. Expected size of cas9 is ~159 kDa.

Figure 5A:
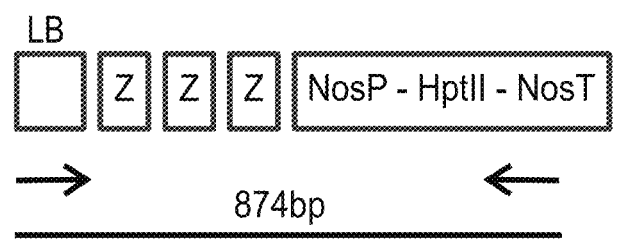
Figure 5B:
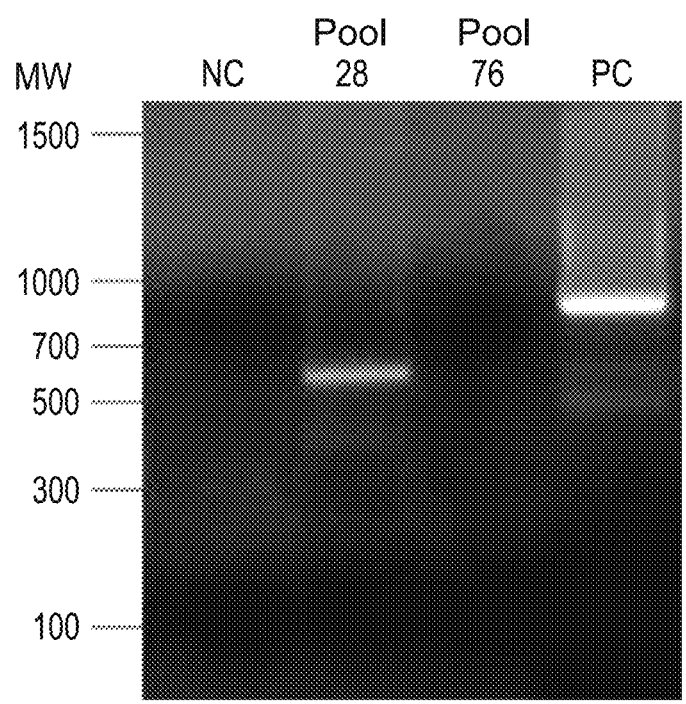

FIGS. 5A-B. PCR assay to detect the functionality of the induced gRNA-Z:Cas9 (A) Schematic description of the primers used for the targets of the left border (LB) and the hptII cassette of the binary vector and the expected size of the PCR product (874 hp). (B). Total genomic DNA extracted from the different cell pools and the PCR products separated on 1% agarose gel. The PCR products from 28 and 76—pools of cells originated from the XylT/FucT knockout cell lines after repeated heat treatments to induce the gRNA-Z expression; N.C—negative control, mix without template; PC—positive control, DNA template produces a 874 bp fragment; MW—molecular weight marker in bp.

Figures 6A, 6B, 6C:
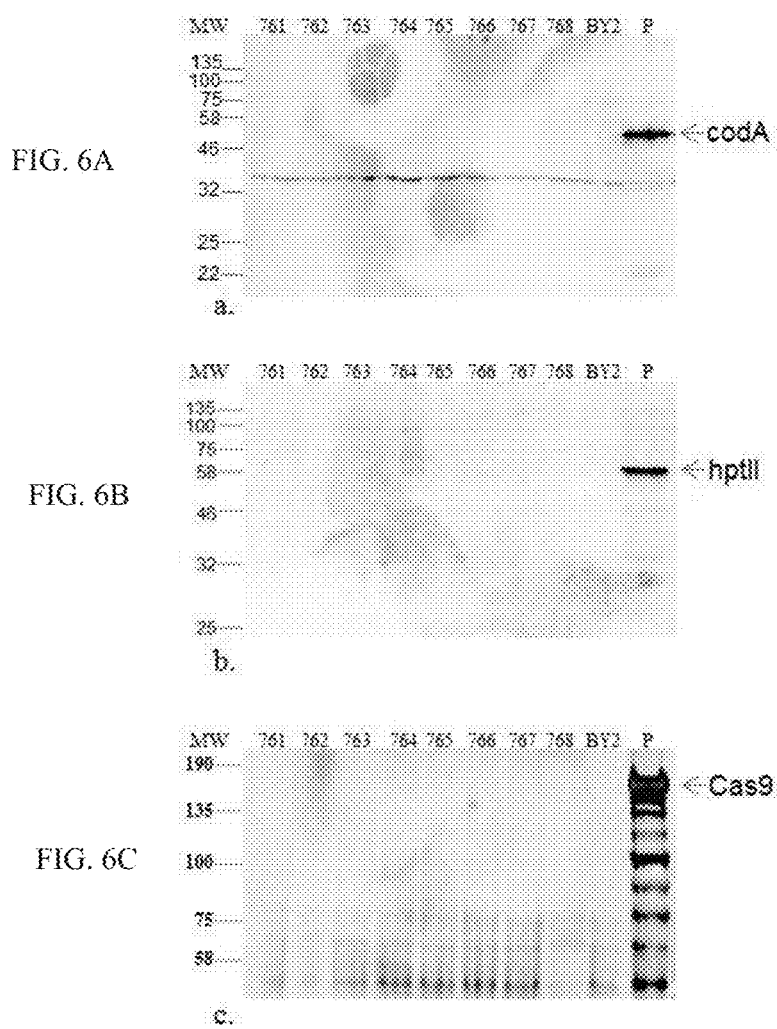

FIGS. 6A-C. Western blot analysis using anti-hptII, anti-Cas9 and anti-codA antibodies Eight clones from the XylT/FucT knockout 76-pool (lines 761-768) were analyzed by Western blot to detect the presence of codA, hptII and Cas9 proteins. A total of 10 µg total protein from each sample were loaded and proteins were separated on SDS-PAGE followed by western blot using (a) anti-codA antibodies (b) anti-hptII antibodies (c) anti-Cas9 antibodies. P—positive control, a cell line that expresses the codA, hptII and Cas9; BY-2—negative control, the non-transgenic BY-2 cells; MW—molecular weight marker in kDa. Blue arrowhead indicates the presence of the relevant protein. Expected size of codA is ~49 kDa. Expected size of hptII is ~39 kDa. Expected size of Cas9 is ~159 kDa.

Figure 7:
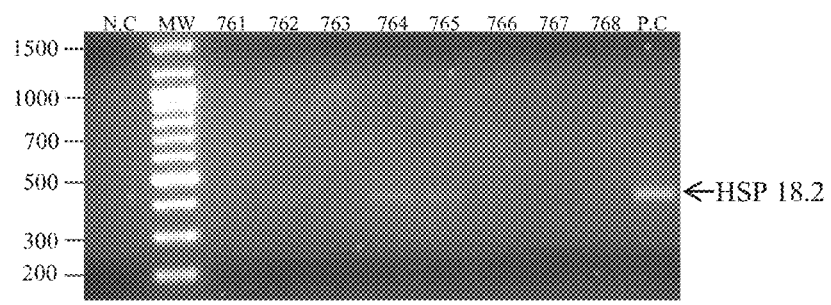

FIG. 7. PCR assay to detect the presence of HSP 18.2 promoter in the re-isolated clones. Total genomic DNA was extracted from eight clones isolated from knockout cell line 76—pool and PCR products were separated on 2% agarose gel. N.C—negative control, mix without template; Lanes 761-768 are isolated clones derived from the 76-pool; P.C—Positive control, mix with DNA extracted from transgenic cell line containing the HSP sequence.

Figure 8A:
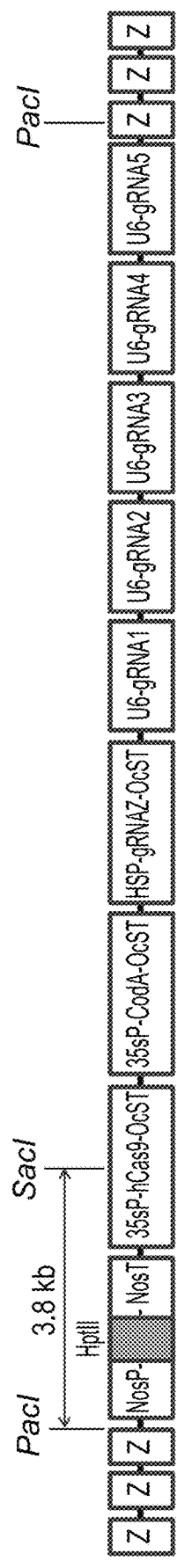
Figure 8B:
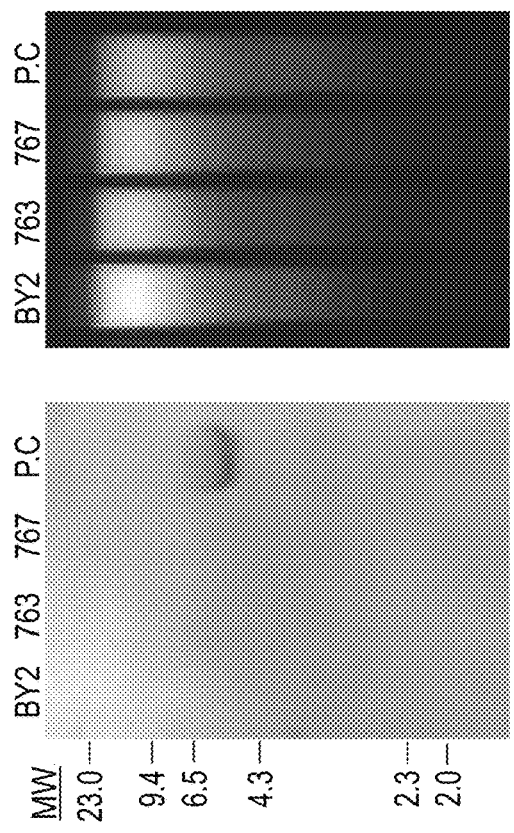

FIGS. 8A-B. Southern blot analysis to confirm excision in lines 763 and 767. (A). Schematic illustration of the T-DNA integrated into the genome and the HptII (orange) probe location. The size of the expected digested fragment is 3.8 kb. (B). On the right, 0.8% agarose gel stained with Ethidium Bromide and transferred onto the membrane for the hybridization. On the left, southern blot analysis of PacI and SacI digested genomic DNA from cells that are wild type (BY2), line 763, line 767 and positive control transgenic BY2 cell line containing the HptII gene (P.C). The expected size of the positive control digested fragment is 6 kb. Hybridization was done with HptII DNA probe. MW—DNA molecular weight in kb.

Figure 9A:
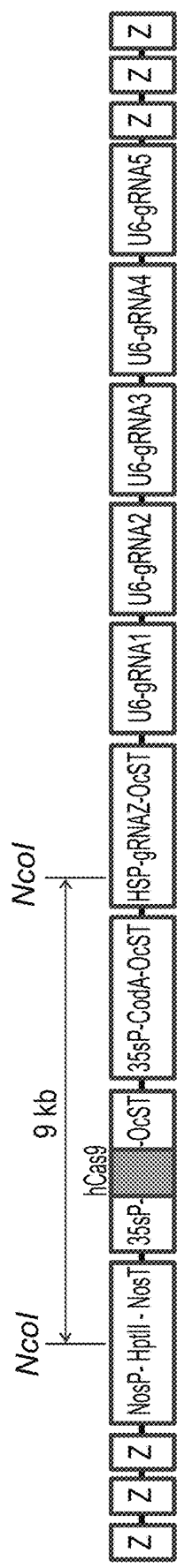
Figure 9B:
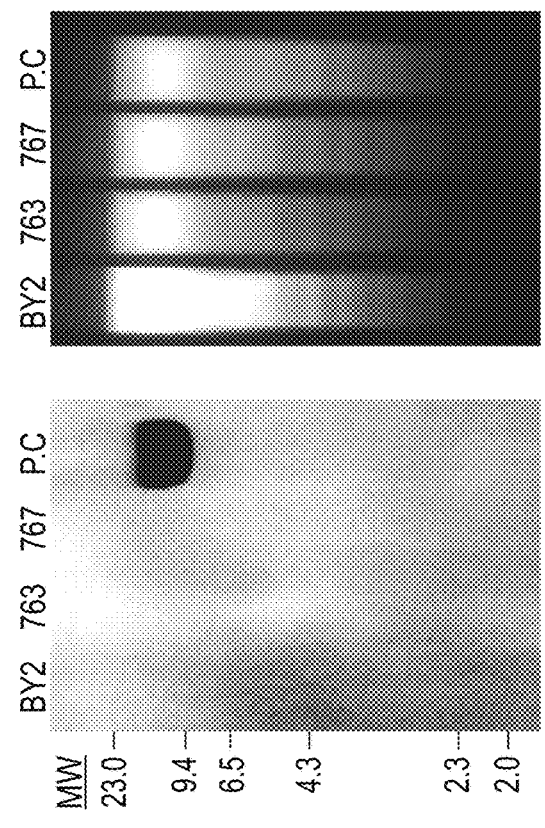

FIGS. 9A-B. Southern blot analysis to confirm excision in lines 763 and 767. (A). Schematic illustration of the T-DNA integrated into the genome and the hCas9 (orange) probe location. The size of the expected digested fragment is 9 kb. (B). On the right, 0.8% agarose gel stained with Ethidium Bromide and transferred onto the membrane for the hybridization. On the left, southern blot analysis of NcoI digested genomic DNA from cells that are wild type (BY2), line 763, line 767 and positive control transgenic BY2 cell line containing the hCas9 gene (P.C). The expected size of the positive control digested fragment is 10.6 kb. Hybridization was done with hCas9 DNA probe. MW—DNA molecular weight in kb.

Figure 10A:
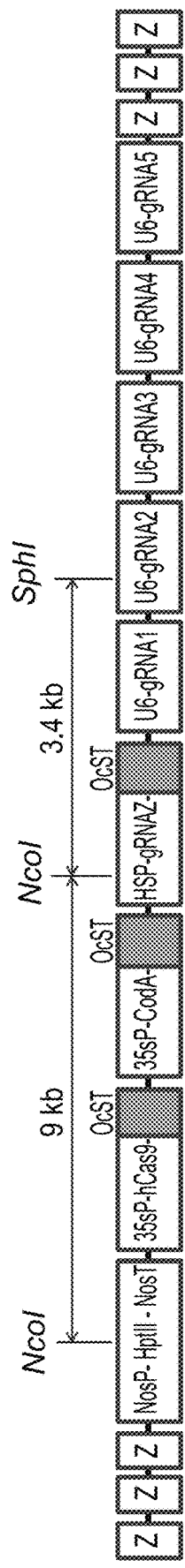
Figure 10B:
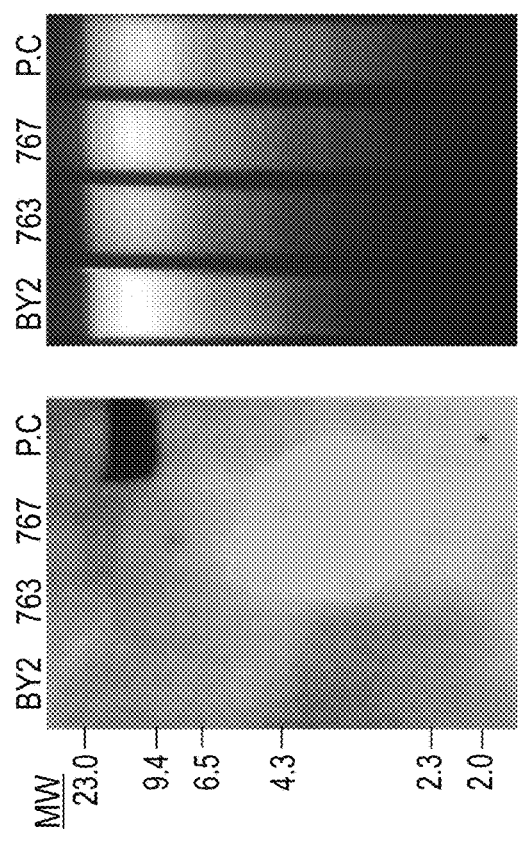

FIGS. 10A-B. Southern blot analysis to confirm excision in lines 763 and 767. (A). Schematic illustration of the T-DNA integrated into the genome and the OcST (orange) probe locations. The sizes of the expected digested fragments are 9 kb and 3.4 kb. (B). On the right, 0.8% agarose gel stained with Ethidium Bromide and transferred onto the membrane for the hybridization. On the left, southern blot analysis of NcoI and SphI digested genomic DNA from cells that are wild type (BY2), line 763, line 767 and positive control transgenic BY2 cell line containing the OcST (P.C). The expected size of the positive control digested fragment is 10.6 kb. Hybridization was done with OcST DNA probe. MW—DNA molecular weight in kb.

Figure 11A:
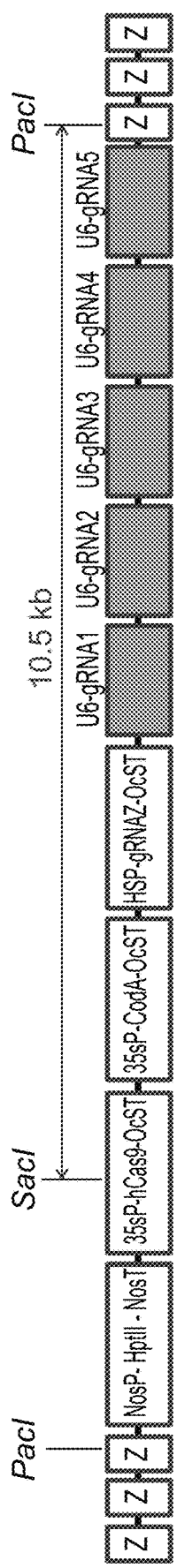
Figure 11B:
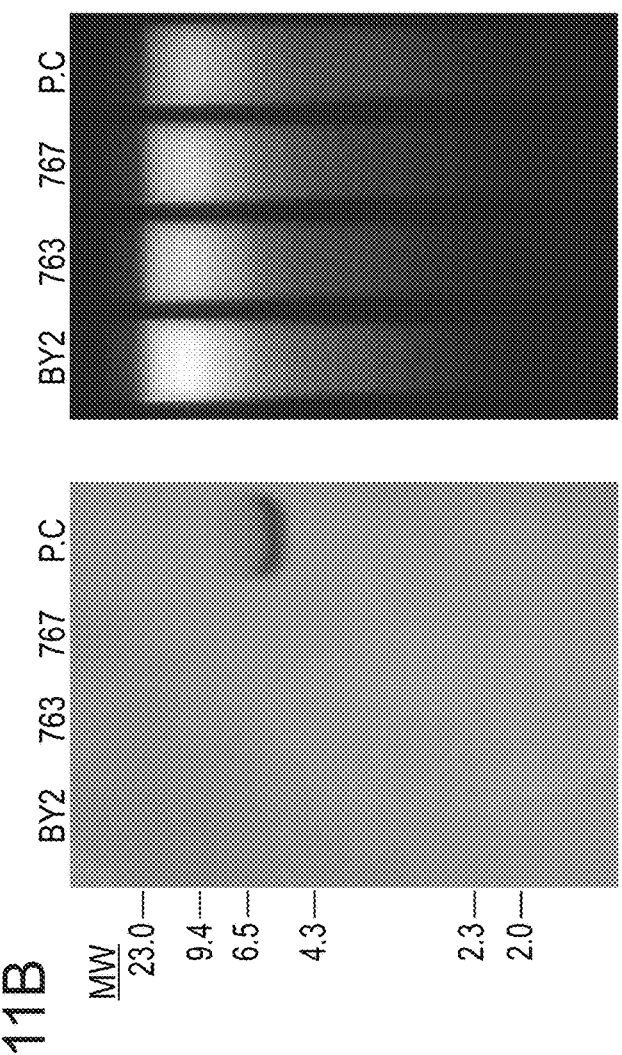

FIGS. 11A-B. Southern blot analysis to confirm excision in lines 763 and 767. (A). Schematic illustration of the T-DNA integrated into the genome and the U6-gRNA (orange) probe locations. The size of the expected digested fragment is 10.5 kb. (B). On the right, 0.8% agarose gel stained with Ethidium Bromide and transferred onto the membrane for the hybridization. On the left, southern blot analysis of SacI and PacI digested genomic DNA from cells that are wild type (BY2), line 763, line 767 and positive control transgenic BY2 cell line containing the U6-gRNA1-5 (P.C). The expected size of the positive control digested fragment is 6 kb. Hybridization was done with mix of U6-gRNA1-5 probes. MW—DNA molecular weight in kb.

FIG. 12 provides details of the DNA sequences selected as the CAS9 targets (crRNAs). Targeted nucleotides (black letters), PAM is present at their 3' end (red letters).
 crRNA1—SEQ ID NO: 24;
 crRNA2—SEQ ID NO: 25;
 crRNA3—SEQ ID NO: 26;
 crRNA4—SEQ ID NO: 27;
 crRNA5—SEQ ID NO: 28.

DESCRIPTION OF SPECIFIC EMBODIMENTS OF THE INVENTION

The present invention, in some embodiments thereof, relates to a method of removing a construct used to transform cells and, more particularly, but not exclusively, to plant cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Heterologous DNA and selectable markers are used for genome editing designated to produce improved host cell lines for overexpression of recombinant biotherapeutic proteins. The removal of these heterologous DNA and selectable markers, no longer needed, can be beneficial since they pose excessive metabolic burden on the cells machinery and may limit their further application in subsequent transformations.

The presence of these genes in GM plants, and subsequently in food, feed and die environment, are of concern and subject to special government regulation in many countries. Various techniques were previously developed for the removal of transgenes and markers while leaving only the required ones in place.

The present inventors have now developed an innovative stepwise methodology in which as a first step, cells are transformed to express an agent which regulates (e.g. up or downregulates expression) or edits (e.g. knocks in or knocks out) a nucleic acid sequence of the genome.

The second step includes the excision of at least a part of the inserted cassette by induction of specific gRNA designed to target at least two sites on the cassette. The first and second step are carried out in one transformation run.

As an example, the present inventors transformed plant cells to express CRISPR-Cas9 and a gRNA which targets a gene of interest. The CRISPR-Cas9 is used sequentially, in the first step to down-regulate expression of a gene of interest, and in the second step to excise the CRISPR-Cas9 cassette. The genome editing step and the transgene removal step are achieved in one transformation run. This mechanism enables CRISPR genome editing leaving no traces of the introduced transgenes.

Whilst reducing the present invention to practice the present inventors used the above described methodology to initially knock-out the β(1,2)-xylosyltranferase (XylT) and the α(1,3)-fucosyltransferase (FucT) genes in *Nicotiana tabacum* L. cv Bright Yellow 2 (BY-2) cell suspension.

The present inventors clearly demonstrated the subsequent removal of the entire T-DNA of 14.3 kb by Western blot analyses, using various antibodies (FIGS. 6A-C), and by Southern blot hybridization (FIGS. 8A-B, 9A-B, 10A-B and 11A-B), using different probes.

The present inventors propose that the highly efficient removal step can be activated at any point of time after the cells' transformation, enabling as much time as required for CRISPR-Cas9 to perform its targeted genes modifications, before self-excision.

Thus, according to a first aspect of the present invention there is provided a nucleic acid construct comprising a nucleic acid sequence which encodes:

(i) at least one nucleic acid agent operatively linked to a first promoter, wherein said agent is for editing or regulating at least one nucleic acid target of interest in an organism or cell of said organism;
(ii) at least one construct-eliminating gRNA;
(iii) a CRISPR endonuclease, wherein either said construct-eliminating gRNA or said CRISPR endonuclease is operatively linked to a second promoter, wherein said first promoter and said second promoter are selected such that initiation of transcription from said second promoter occurs following initiation of transcription from said first promoter in said organism or said cell of said organism; and
(iv) at least two copies of a target sequence for said construct-eliminating gRNA.

The nucleic acid construct of some embodiments of the invention comprises a polynucleotide sequence encoding the above mentioned components. Such a nucleic acid construct includes a promoter sequence for directing transcription of the polynucleotide sequence in the cell in a constitutive or inducible manner, as further described herein below. Preferably, the promoter utilized by the nucleic acid construct of some embodiments of the invention is active in the specific cell population transformed.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In the construction of the nucleic acid construct, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids hearing these viral replicons are replicated episomally as long as the appropriate factors are provided by genes either carried on the plasmid or with the genome of the host cell.

The nucleic acid construct may or may not include a eukaryotic replicon. If a eukaryotic replicon is present, then the vector is amplifiable in eukaryotic cells using the appropriate selectable marker. If the nucleic acid construct does not comprise a eukaryotic replicon, no episomal amplification is possible. Instead, the recombinant DNA integrates into the genome of the engineered cell, where the promoter directs expression of the desired nucleic acid.

The nucleic acid construct of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the nucleic acid construct can be arranged in a variety of configurations. For example, enhancer elements, promoters and the like, and even the polynucleotide sequence(s) encoding a nucleic acid silencing agent can be arranged in a "head-to-tail" configuration, may be present as an inverted complement, or in a complementary configuration, as an anti-parallel strand. While such variety of configuration is more likely to occur with non-coding elements of the nucleic acid construct, alternative configurations of the coding sequence within the nucleic acid construct are also envisioned.

Examples of nucleic acid constructs for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Examples of plant expression vectors include pBI01, pBI101.2, pBI101.3, pBI121 and pBIN19 (Clontech).

Examples of bacterial constructs include the pET series of E. coli expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

Nucleic acid constructs containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Constructs useful in the methods according to some embodiments of the invention may be constructed using recombinant DNA technology well known to persons skilled in the art. The construct may be commercially available, suitable for transforming into organisms (e.g. plants) and suitable for expression in the transformed cells.

The nucleic acid agent of this aspect of the present invention is for editing or regulating expression of at least one nucleic acid target of interest in an organism or cell of said organism.

In one embodiment, the nucleic acid agent is a DNA editing agent.

As used herein "a DNA editing agent" refers to a single stranded or double stranded engineered DNA endonuclease and in certain embodiments ancillary agents (e.g., gRNA(s), donor DNA sequences) causing insertion, deletion, insertion-deletion, substitution, insertion, or any combination thereof in a genome of a cell.

In one embodiment, the nucleic acid agent is a nucleic acid silencing agent.

As used herein "nucleic acid silencing agent" refers to a nucleic acid molecule which downregulates gene expression in a specific manner, acting either at the DNA (genomic) level or RNA level. Examples of nucleic acid silencing agents include but are not limited to siRNA, antisense oligonucleotides, ribozymes and DNA editing agents which affect expression of genes.

It will be appreciated that when a DNA editing agent downregulates gene expression, the DNA editing agent may also be referred to as a nucleic acid silencing agent.

Those skilled in the art will be aware of whether expression is inhibited, interrupted or reduced, without undue experimentation. For example, the level of expression of a particular gene may be determined by polymerase chain reaction (PCR) following reverse transcription of an mRNA template molecule. Alternatively, the expression level of a genetic sequence may be determined by northern hybridisation analysis or dot-blot hybridisation analysis or in situ hybridisation analysis or similar technique, wherein mRNA is transferred to a membrane support and hybridised to a "probe" molecule which comprises a nucleotide sequence complementary to the nucleotide sequence of the mRNA transcript encoded by the gene-of-interest, labeled with a suitable reporter molecule such as a radioactively-labelled dNTP (e.g., [alpha-32P] dCTP or [alpha-35S] dCTP) or biotinylated dNTP, amongst others. Expression of the polypeptide-of-interest may then be determined by detecting the appearance of a signal produced by the reporter molecule bound to the hybridised probe molecule.

Alternatively, the rate of transcription of a particular gene may be determined by nuclear run-on and/or nuclear run-off experiments, wherein nuclei are isolated from a particular cell or tissue and the rate of incorporation of rNTPs into specific mRNA molecules is determined. Alternatively, the expression of the gene-of-interest may be determined by RNase protection assay, wherein a labelled RNA probe or "riboprobe" which is complementary to the nucleotide sequence of mRNA encoded by said gene-of-interest is annealed to said mRNA for a time and under conditions sufficient for a double-stranded mRNA molecule to form, after which time the sample is subjected to digestion by RNase to remove single-stranded RNA molecules and in particular, to remove excess unhybridised riboprobe. Such approaches are described in detail by Sambrook, J., Fritsch, E. F. and Maniatis, T. Molecular Cloning: a laboratory manual. 2nd ed. N.Y., Cold Spring Harbor Laboratory, Cold Spring Harbor Laboratory Press, 1989. 1659 p. ISBN 0-87969-309-6.

Those skilled in the art will also be aware of various immunological and enzymatic methods for detecting the level of expression of a particular gene at the protein level, for example using rocket immunoelectrophoresis, ELISA, radioimmunoassay and western blot immunoelectrophoresis techniques, amongst others.

Throughout the disclosure it is submitted that a "nucleic acid agent" refers to one or more nucleic acid agents.

According to a specific embodiment, the nucleic acid agent (e.g. silencing agent) is directed to a single target sequence of interest.

According to a specific embodiment, the silencing agent is directed to a plurality of target sequences of interest (e.g., 2, 3, 4, 5, 6 or 7).

According to a specific embodiment, the nucleic acid agent (e.g. silencing agent) modifies the target genes (or RNA thereof) but not other genes in the genome of the organism (e.g. in the N. tabacum genome or expression products thereof).

Thus, according to a specific embodiment, the nucleic acid silencing agent modifies the target sequence of interest (e.g. FucT and/or XylT) and is devoid of "off target" activity, e.g., does not modify other sequences in the N. tabacum genome.

According to other embodiments, the silencing agent modifies the target sequence of interest (in the target genome, i.e., N. tabacum) and is significantly reduced in "off target" activity. Significant reductions in "off target" activity include reductions of off target modification rates to less than 2%, 1%, or 0.1%. Methods that can be used to assess off target modification rates include those of Haeussler et al. (Genome Biology, 2016, 17:148).

According to a specific embodiment, the nucleic acid silencing agent (e.g., DNA editing agent) comprises an "off target activity" on a non-essential gene in the target genome.

"Non-essential" refers to a gene that when modified (or expression product thereof) by the nucleic acid silencing agent does not affect the phenotype of the target genome, such as cell proliferation, stress tolerance and the like.

Off-target effects can be assayed using methods which are well known in the art.

As mentioned, the nucleic acid silencing agent can act at the RNA level. Following is a non-limiting description of silencing methods that can be used in accordance with some embodiments.

Sense suppression or co-suppression—In some embodiments of the invention, inhibition of the expression of target polypeptide may be obtained by sense suppression or co-suppression. For co-suppression, an expression cassette is designed to express an RNA molecule corresponding to all or part of a messenger RNA encoding a target polypeptide in the "sense" orientation. Over-expression of the RNA molecule can result in reduced expression of the native gene. Accordingly, multiple cell lines transformed with the co-suppression expression cassette are screened to identify those that show the greatest inhibition of target polypeptide expression.

The polynucleotide used for co-suppression may correspond to all or part of the sequence encoding the target polypeptide, all or part of the 5' and/or 3' untranslated region of a target transcript, or all or part of both the coding sequence and the untranslated regions of a transcript encoding the target polypeptide. In some embodiments where the polynucleotide comprises all or part of the coding region for the target polypeptide, the expression cassette is designed to eliminate the start codon of the polynucleotide so that no protein product will be transcribed.

Co-suppression may be used to inhibit the expression of plant genes (e.g. plant genes) to produce cells (e.g. plant cells) having undetectable protein levels for the proteins encoded by these genes. See, for example, Broin, et al., (2002) Plant Cell 15:1517-1532. Co-suppression may also be used to inhibit the expression of multiple proteins in the same cell. Methods for using co-suppression to inhibit the expression of endogenous genes in plants are described in Flavell, et al., (1995) Proc. Natl. Acad. Sci. USA 91:3590-3596; Jorgensen, et al., (1996) Plant Mol. Biol. 31:957-973; Johansen and Carrington, (2001) Plant Physiol. 126:930-938; Broin, et al., (2002) Plant Cell 15:1517-1532; Stoutjesdijk, et al., (2002) Plant Physiol. 129:1723-1731; Yu, et al., (2003) Phytochemistry 63:753-763; and U.S. Pat. Nos. 5,035,323, 5,283,185 and 5,952,657; each of which is herein incorporated by reference. The efficiency of co-suppression may be increased by including a poly-dt region in the expression cassette at a position 3' to the sense sequence and 5' of the polyadenylation signal. See, US Patent Publication Number 20020058815, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,185 and 5,035,323; herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing. (Aufsatz, et al., (2002) PNAS 99(4):16499-16506; Mette, et al., (2000) EMBO J. 19(19):5194-5201).

Antisense Suppression—In some embodiments of the invention, inhibition of the expression of the target gene may be obtained by antisense suppression. For antisense suppression, the expression cassette is designed to express an RNA molecule complementary to all or part of a messenger RNA encoding the target polypeptide. Over-expression of the antisense RNA molecule can result in reduced expression of the native gene. Accordingly, multiple cell lines transformed with the antisense suppression expression cassette are screened to identify those that show the greatest inhibition of target polypeptide expression.

The polynucleotide for use in antisense suppression may correspond to all or part of the complement of the sequence encoding the target polypeptide, all or part of the complement of the 5' and/or 3' untranslated region of the target polypeptide transcript, or all or part of the complement of both the coding sequence and the untranslated regions of a transcript encoding the target polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same cell. Furthermore, portions of the antisense nucleotides may be used to disrupt the expression of the target gene. Generally, sequences of at least 50 nucleotides, 100 nucleotides, 200 nucleotides, 300, 500, 550, 500, 550 or greater may be used. Methods for using antisense suppression to inhibit the expression of endogenous genes in plants are described, for example, in Liu, et al., (2002) Plant Physiol. 129:1732-1753 and U.S. Pat. No. 5,759,829, which is herein incorporated by reference.

Efficiency of antisense suppression may be increased by including a poly-dt region in the expression cassette at a position 3' to the antisense sequence and 5' of the polyadenylation signal. See, US Patent Publication Number 20020058815.

Double-Stranded RNA Interference—In some embodiments of the invention, inhibition of the expression of a target polypeptide may be obtained by double-stranded RNA (dsRNA) interference. For dsRNA interference, a sense RNA molecule like that described above for co-suppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple cell lines transformed with the dsRNA interference expression cassette or expression cassettes are then screened to identify cell lines that show the greatest inhibition of target polypeptide expression. Methods for using dsRNA interference to inhibit the expression of endogenous plant genes are described in Waterhouse, et al., (1998) Proc. Natl. Acad. Sci. USA 95:13959-13965, Liu, et al., (2002) Plant Physiol. 129:1732-1753, and WO 99/59029, WO 99/53050, WO 99/61631, and WO 00/59035;

Hairpin RNA Interference and Intron-Containing Hairpin RNA Interference—In some embodiments of the invention, inhibition of the expression of one or more target polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) Nat. Rev. Genet. 5:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz, (2000) Proc. Natl. Acad. Sci. USA 97:5985-5990; Stoutjesdijk, et al., (2002) Plant Physiol. 129:1723-1731; and Waterhouse and Helliwell, (2003) Nat. Rev. Genet. 5:29-38. Methods for using hpRNA interference to inhibit or silence the expression of genes are described, for example, in Chuang and Meyerowitz, (2000) Proc. Natl. Acad. Sci. USA 97:5985-5990; Stoutjesdijk, et al., (2002) Plant Physiol. 129:1723-1731; Waterhouse and Helliwell, (2003) Nat. Rev. Genet. 5:29-38; Pandolfini, et al., BMC Biotechnology 3:7, and US Patent Publication Number 20030175965; each of which is herein incorporated by reference. A transient assay for the efficiency of hpRNA constructs to silence gene expression in vivo has been described by Panstruga, et al., (2003) Mol. Biol. Rep. 30:135-150, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) Nature 507:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) Nature 507:319-320; Wesley, et al., (2001) Plant J. 27:581-590; Wang and Waterhouse, (2001) Curr. Opin. Plant Biol. 5:156-150; Waterhouse and Helliwell, (2003) Nat. Rev. Genet. 5:29-38; Helliwell and Waterhouse, (2003) Methods 30:289-295, and US Patent Publication Number 20030180955, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00905, herein incorporated by reference.

Amplicon-Mediated Interference—Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for target polypeptide). Methods of using amplicons to inhibit the expression of endogenous plant genes are described, for example, in Angell and Baulcombe, (1997) EMBO J. 16:3675-3685, Angell and Baulcombe, (1999) Plant J. 20:357-362, and U.S. Pat. No. 6,656,805, each of which is herein incorporated by reference.

Ribozymes—In some embodiments, the polynucleotide expressed by the expression cassette of the invention is catalytic RNA or has ribozyme activity specific for the messenger RNA of target polypeptide. Thus, the polynucleotide causes the degradation of the endogenous messenger RNA, resulting in reduced expression of the target polypeptide. This method is described, for example, in U.S. Pat. No. 5,987,071, herein incorporated by reference.

Following is a description of various non-limiting examples of methods and DNA editing agents used to downregulate a gene of interest (or to introduce nucleic acid alterations to a gene of interest) and agents for implementing same that can be used according to specific embodiments of the present disclosure.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDS) and non-homologous end-joining (NHEJF). NHEJF directly joins the DNA ends in a double-stranded break, while HDR utilizes a homologous donor sequence as a template for regenerating the missing DNA sequence at the break point. In order to introduce specific nucleotide modifications to the genomic DNA, a donor DNA repair template containing the desired sequence must be present during HDR.

Genome editing cannot be performed using traditional restriction endonucleases since most restriction enzymes recognize a few base pairs on the DNA as their target and these sequences often will be found in many locations across the genome resulting in multiple cuts which are not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location.

This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence.

Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. No. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the non-homologous end-joining (NHEJ) pathway often results in small deletions or small sequence insertions. Since each repair made by NHEJ is unique, the use of a single nuclease pair can produce an allelic series with a range of different deletions at the target site.

The deletions typically range anywhere from a few base pairs to a few hundred base pairs in length, but larger deletions have been successfully generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers are typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

T-GEE system (TargetGene's Genome Editing Engine)—A programmable nucleoprotein molecular complex containing a polypeptide moiety and a specificity conferring nucleic acid (SCNA) which assembles in-vivo, in a target cell, and is capable of interacting with the predetermined target nucleic acid sequence is provided. The programmable nucleoprotein molecular complex is capable of specifically modifying and/or editing a target site within the target nucleic acid sequence and/or modifying the function of the target nucleic acid sequence. Nucleoprotein composition comprises (a) polynucleotide molecule encoding a chimeric polypeptide and comprising (i) a functional domain capable of modifying the target site, and (ii) a linking domain that is capable of interacting with a specificity conferring nucleic acid, and (b) specificity conferring nucleic acid (SCNA) comprising (i) a nucleotide sequence complementary to a region of the target nucleic acid flanking the target site, and (ii) a recognition region capable of specifically attaching to the linking domain of the polypeptide. The composition enables modifying a predetermined nucleic acid sequence target precisely, reliably and cost-effectively with high specificity and binding capabilities of molecular complex to the target nucleic acid through base-pairing of specificity-conferring nucleic acid and a target nucleic acid. The composition is less genotoxic, modular in their assembly, utilize single platform without customization, practical for independent use outside of specialized core-facilities, and has shorter development time frame and reduced costs.

CRISPR-Cas system (also referred to herein as "CRISPR")—Many bacteria and archea contain endogenous RNA-based adaptive immune systems that can degrade nucleic acids of invading phages and plasmids. These systems consist of clustered regularly interspaced short palindromic repeat (CRISPR) nucleotide sequences that produce RNA components and CRISPR associated (Cas) genes that encode protein components. The CRISPR RNAs (crRNAs) contain short stretches of homology to the DNA of specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et at *Science* (2012) 337: 816-821.).

It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et at, 2013; DiCarlo et at, 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded breaks produced by CRISPR/Cas can undergo homologous recombination or NHEJ and are susceptible to specific sequence modification during DNA repair.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs. This creates a system that can be readily modified to target modifications at different genomic sites and/or to target different modifications at the same site. Additionally, protocols have been established which enable simultaneous targeting of multiple genes. The majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

In order to cut DNA at a specific site, Cas9 proteins require the presence of a gRNA and a protospacer adjacent motif (PAM), which immediately follows the gRNA target sequence in the targeted polynucleotide gene sequence. The PAM is located at the 3' end of the gRNA target sequence but is not part of the gRNA. Different Cas proteins require a different PAM. Accordingly, selection of a specific polynucleotide gRNA target sequence by a gRNA is generally based on the recombinant Cas protein used. The PAM for the S. pyogenes Cas9 CRISPR system is 5-NRG-3', where R is either A or G, and characterizes the specificity of this system in human cells. The PAM of S. aureus is NNGRR (SEQ ID NO: 15). The Streptococcus pyogenes Type II system naturally prefers to use an "NGG" sequence, where "N" can be any nucleotide, but also accepts other PAM sequences, such as "NAG" in engineered systems. Similarly, the Cas9 derived from Neisseria meningitidis (NmCas9) normally has a native PAM of NNNNGATT (SEQ ID NO: 16), but has activity across a variety of PAMs, including a highly degenerate NNNNGNNN (SEQ ID NO: 17) PAM.

The gRNA comprises a "gRNA guide sequence" or "gRNA target sequence" which corresponds to the target sequence on the target polynucleotide gene sequence that is followed by a PAM sequence.

The gRNA may comprise a "G" at the 5'end of the polynucleotide sequence. The presence of a "G" in 5' is preferred when the gRNA is expressed under the control of the U6 promoter. The CRISPR/Cas9 system of the present invention may use gRNA of varying lengths. The gRNA may comprise at least a 10 nts, at least 11 nts, at least a 12 nts, at least a 13 nts, at least a 14 nts, at least a 15 nts, at least a 16 nts, at least a 17 nts, at least a 18 nts, at least a 19 nts, at least a 20 nts, at least a 21 nts, at least a 22 nts, at least a 23 nts, at least a 24 nts, at least a 25 nts, at least a 30 nts, or at least a 35 nts of the target caspase 6 DNA sequence which is followed by a PAM sequence. The "gRNA guide sequence" or "gRNA target sequence" may be at least 17 nucleotides (17, 18, 19, 20, 21, 22, 23), preferably between 17 and 30 nts long, more preferably between 18-22 nucleotides long. In an embodiment, gRNA guide sequence is between 10-40, 10-30, 12-30, 15-30, 18-30, or 10-22 nucleotides long. The PAM sequence may be "NGG", where "N" can be any nucleotide. gRNA may target any region of the target gene which is immediately upstream (contiguous, adjoining, in 5') to a PAM (e.g., NGG) sequence.

Although a perfect match between the gRNA guide sequence and the DNA sequence on the targeted gene is preferred, a mismatch between a gRNA guide sequence and target sequence on the gene sequence of interest is also permitted as along as it still allows hybridization of the gRNA with the complementary strand of the gRNA target polynucleotide sequence on the targeted gene. A seed sequence of between 8-12 consecutive nucleotides in the gRNA, which perfectly matches a corresponding portion of the gRNA target sequence is preferred for proper recognition of the target sequence. The remainder of the guide sequence may comprise one or more mismatches. In general, gRNA activity is inversely correlated with the number of mismatches. Preferably, the gRNA of the present invention comprises 7 mismatches, 6 mismatches, 5 mismatches, 4 mismatches, 3 mismatches, more preferably 2 mismatches, or less, and even more preferably no mismatch, with the corresponding gRNA target gene sequence (less the PAM). Preferably, the gRNA nucleic acid sequence is at least 90%, 91%, 92%, 93%, 94%, 95%, 96%, 97%, 98% and 99% identical to the gRNA target polynucleotide sequence in the gene of interest. Of course, the smaller the number of nucleotides in the gRNA guide sequence the smaller the number of mismatches tolerated. The binding affinity is thought to depend on the sum of matching gRNA-DNA combinations.

Any gRNA guide sequence can be selected in the target nucleic acid sequence, as long as it allows introducing at the proper location, the patch/donor sequence of the present invention.

Accordingly, the gRNA guide sequence or target sequence of the present invention may be in coding or non-coding regions a gene (i.e., introns or exons).

In one embodiment, the gRNA is a sgRNA.

As used herein, the term "sgRNA" refers to single guide RNA used in conjunction with CRISPR associated systems (Cas). sgRNAs are a fusion of crRNA and tracrRNA and contain nucleotides of sequence complementary to the desired target site. Jinek et al., "A programmable dual-RNA-guided DNA endonuclease in adaptive bacterial immunity" Science 337(6096):816-821 (2012) Watson-Crick pairing of the sgRNA with the target site permits R-loop formation, which in conjunction with a functional PAM permits DNA cleavage or in the case of nuclease-deficient Cas9 allows binds to the DNA at that locus.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

Non-limiting examples of a gRNA that can be used in the present disclosure include those described in the Example section which follows.

In order to use the CRISPR system, both gRNA and a CAS endonuclease (e.g. Cas9) should be expressed in a target cell. The insertion vector can contain both cassettes on a single plasmid or the cassettes are expressed from two separate plasmids. CRISPR plasmids are commercially available such as the px330 plasmid from Addgene (75 Sidney St. Suite 550A•Cambridge, MA 02139). Use of clustered regularly interspaced short palindromic repeats (CRISPR)-associated (Cas)-guide RNA technology and a Cas endonuclease for modifying plant genomes are also at least disclosed by Svitashev et al., 2015, Plant Physiology, 169 (2): 931-945; Kumar and Jain, 2015, J Exp Bot 66: 47-57; and in U.S. Patent Application Publication No. 20150082478, which is specifically incorporated herein by reference in its entirety. CAS endonucleases that can be used to effect DNA editing with gRNA include, but are not limited to, Cas9, CasX, Cpf1 (Zetsche et al., 2015, Cell. 163(3):759-71), C2c1, C2c2, and C2c3 (Shmakov et al., Mol Cell. 2015 Nov. 5; 60(3):385-97).

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

The nucleic acid agent of this aspect of the present invention may target any nucleic acid of interest.

In one embodiment, the nucleic acid of interest is a regulatory region of a gene. In another embodiment, the nucleic acid of interest is the protein coding region of a gene.

According to a particular embodiment, the gene of interest is a glycosylating enzyme.

Examples of glycosylating enzymes comprises xylosyltransferase and/or fucosyltransferase.

As used herein "Xylosyltransferase" abbreviated as "XylT" refers to an enzyme that catalyzes the transfer of xylose from GDP-xylose to the beta-linked bisecting mannose in the core of N-glycans while linking it with a beta-1,2 glycosidic linkages (EC 2.4.2.38).

As used herein "Fucosyltransferase", abbreviated as "FucT" refers to an enzyme that catalyses the transfer of fucose from GDP-fucose to the core alpha-linked N-acetyl glucosamine (GlcNAc) of protein-bound N-glycans (EC 2.4.1.214).

The *N. tabacum* comprises two XylT genes and 5 FucT genes. These include:
  Ntab-BX_AWOK-SS596 (Ntab-XylT-A, SEQ ID NO: 18);
  Ntab-BX_AWOK-SS12784 (Ntab-XylT-B, SEQ ID NO: 19).
  Ntab-K326_AWOJ-SS19752 (Ntab-FucT-A, SEQ ID NO: 20)
  Ntab-BX_AWOK-SS16887 (Ntab-FucT-B, SEQ ID NO: 20).
  Ntab-K326_AWOJ-SS16744 (Ntab-FucT-C, SEQ ID NO: 21).
  Ntab-K326_AWOJ-SS19661 (Ntab-FucT-D, SEQ ID NO: 22)
  Ntab-K326_AWOJ-SS19849 (Ntab-FucT-E, SEQ ID NO: 23).

Exemplary crRNA sequences which may be used to silence the above mentioned gene I are described in FIG. 12.

As mentioned, the nucleic acid construct of this aspect of the present invention further encodes a gRNA (referred to herein as the "construct-eliminating gRNA") and a CRISPR endonuclease. Each of these components have been described herein above.

As used herein the term "construct eliminating gRNA" refers to a gRNA sequence that specifically targets at least one sequence on the construct itself and does not target a genomic sequence of the transformed cell. The construct eliminating gRNA does not necessarily serve to eliminate (or excise) the entire sequence of the construct, but rather at least a portion of the construct, as further described herein below.

As mentioned the nucleic acid agent of the present invention is operatively linked to a first promoter. The promoter is selected according to the cell which is being transformed and such that expression therefrom takes places before expression from the second promoter (as further described herein).

According to a particular embodiment, the cell type being transformed is a plant cell. For this embodiment, plant-expressible promoters are contemplated.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

This includes any promoter of plant origin, but also any promoter of non-plant origin which is capable of directing transcription in a plant cell, i.e., certain promoters of viral or bacterial origin such as the CaMV35S (Harpster et al. (1988) Mol Gen Genet. 212(1):182-90, type III RNA polymerase III promoter (U6), the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) Plant Cell 8(1):15-30), stem-specific promoters (Keller et al., (1988) EMBO J. 7(12): 3625-3633), leaf specific promoters (Hudspeth et al. (1989) Plant Mol Biol. 12: 579-589), mesophyl-specific promoters, root-specific promoters (Keller et al. (1989) Genes Dev. 3: 1639-1646), tuber-specific promoters (Keil et al. (1989) EMBO J. 8(5): 1323-

1330), vascular tissue specific promoters (Peleman et al. (1989) Gene 84: 359-369), stamen-selective promoters (WO 89/10396, WO 92/13956), dehiscence zone specific promoters (WO 97/13865) and the like.

As mentioned, the promoter which is operatively linked to the nucleic acid agent (referred to herein as the first promoter) is selected such that initiation of transcription therefrom occurs prior to initiation of transcription from said second promoter (which is operatively linked to a CRISPR endonuclease or the construct-eliminating gRNA).

In order to bring about sequential activation of promoters (without performing a separate transformation step), the present inventors contemplate use of particular pairs of promoters.

For example, in one instance the first promoter is a constitutive promoter and the second promoter is an inducible promoter.

Examples of constitutive promoters include, but are not limited to viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311].

Examples of inducible promoters include, but are not limited to light inducible promoters, heat shock promoters, e.g., soybean hsp17.5-E or hsp17.3-B [Gurley et al. (1986) Mol. Cell. Biol. 6:559-565], tetracycline-inducible promoter (Zabala M, et al., Cancer Res. 2004, 64(8): 2799-804).

According to a specific embodiment, the inducible promoter comprises a heat shock promoter.

According to a specific embodiment, the nucleic acid agent comprises a CRISPR and the construct comprises at least one gRNA (which binds to the target gene of interest) operatively linked to a constitutive promoter (e.g. a type III RNA polymerase III promoter such as U6) and a CRISPR endonuclease operatively linked to a constitutive promoter (e.g. 35S promoter). The construct further comprises a construct removing gRNA which is operatively linked to an inducible promoter (e.g. heat shock promoter).

As another example, both the first and the second promoter may be non-identical inducible promoters.

As another example, the first promoter may be one which is activated at an earlier stage during development of an organism (e.g. plant)—i.e. promoters that are developmentally staggered.

The phrase "plant developmental stage-specific promoter" refers to a promoter that is expressed not constitutively but at specific plant developmental stage or stages Plant development goes through different stages and in the context of this invention the germline goes different developmental stages starting from fertilization through development of embryo, vegetative shoot apical meristem, floral shoot apical meristem, anther and pistil primordia. anther and pistil, micro- and macrospore mother cells, and macrospore (egg) and microspore (pollen).

Examples of plant developmental stage specific promoters are disclosed in PCT International number WO2001036595A2, the contents of which are incorporated herein. One of ordinary skill in the art would be able to select pairs of promoters that are activated in a staggered timeline.

As another example, the first promoter may be a strong promoter and the second promoter a weak promoter such that the first promoter is activated prior to the activation of the second promoter.

An exemplary strong promoter for expression in yeast is the ADH2/GAPDH promoter. An exemplary weak promoter for expression in yeast is the YPTI constitutively active promoter. See, Sears et al., Yeast 14:783-790 (1998). A strong promoter for expression in mammalian cells is the CMV promoter. An exemplary strong promoter for expression in bacteria is the recA promoter. An exemplary weak promoter for expression in bacteria is the araBAD promoter. Examples of strong promotors in plants include cauliflower mosaic virus 35S; actin promoter; ubiquitin promoter. Examples of weak promotor in plants include nopaline synthase (nos) promoter; G10-90 promoter.

It will be appreciated that when the nucleic acid agent does not comprise a CRISPR component, then either the construct eliminating gRNA and/or the CRISPR endonuclease may be operatively linked to the second type of promoter (i.e. one which is activated after activation of the promoter linked to the nucleic acid agent). On the other hand, when the nucleic acid agent does comprise CRISPR components, then only the construct eliminating gRNA is operatively linked to the second type of promoter, and the CRISPR endonuclease is operatively linked to the first type of promoter.

The nucleic acid construct of this aspect of the present invention further comprises at least two copies of a target sequence for said construct-eliminating gRNA.

The at least two copies of the target sequence are positioned such that they flank the part of the construct that is to be subsequently excised. Thus, for example if it is desirable that only a selection marker which is present on the construct is removed, then the position of the target sequences is such that they flank the sequence which encodes the selection marker. If it is desirable that the full construct is removed, then the position of the target sequences is such they flank the entire insert (e.g. on a TDNA vector the target sequence may be positioned immediately downstream to the left border and immediately upstream of the right border—see for example FIG. 1). It will be appreciated that more than one copy of the target sequence can be used in the construct. Thus, for example, the present inventors contemplate at least two, three, four or more copies of the target sequence positioned immediately upstream of the sequence which is to be eliminated and at least two, three, four or more copies of the target sequence positioned immediately upstream of the sequence which is to be eliminated. Preferably, the multiple copies are positioned in tandem.

As mentioned, the nucleic acid construct of the present invention may optionally include a positive and/or negative selectable marker. Typically, the markers are placed under control of the first type of promoter (e.g. constitutive or strong promoter), examples of which are further detailed herein above.

A "positive selectable marker gene" as used herein, refers to a protein that allows growth on selective medium of cells that carry the marker gene, but not of cells that do not carry the marker gene. Selection is for cells that grow on the selective medium (showing acquisition of the marker) and is used to identify transformants. A common example is a drug-resistance marker such as NPT (neomycin phosphotransferase), whose gene product detoxifies kanamycin by phosphorylation and thus allows growth on media containing the drug. Other positive selectable marker genes for use in connection with the present invention include, but are not limited to, a hygromycin phosphotransferase gene (Waldron et al, Plant Mol. Biol. 5: 103-108) which codes for hygromycin resistance and can be selected for using hygromycin; neo gene (Potrykus et al., 1985), which codes for kanamycin resistance and can be selected for using kanamycin, G418, etc.; a bar gene, which codes for bialaphos (basta) resistance; a mutant aroA gene, which encodes an altered EPSP synthase protein (Hinchee et al., 1988), thus conferring glyphosate resistance; a nitrilase gene such as bxn from *Klebsiella ozaenae*, which confers resistance to bromoxynil (Stalker et al., 1988); a mutant acetolactate synthase gene (ALS), which confers resistance to imidazolinone, sulfonylurea or other ALS inhibiting chemicals (European Patent Application 154,204, 1985); a methotrexate resistant DHFR gene (Thillet et al., 1988), or a dalapon dehalogenase gene that confers resistance to the herbicide dalapon; the pat gene from *Streptomyces viridochromogenes*, which encodes the enzyme phosphinothricin acetyl transferase (PAT) and inactivates the active ingredient in the herbicide bialaphos, phosphinothricin (PPT); or a mutated anthranilate synthase gene that confers resistance to 5-methyl tryptophan.

The phrase "negative selectable marker gene" refers to a protein that prevents the growth of a cell on selective medium of cells that carry the marker gene, but not of cells that do not carry the marker gene. Selection of cells that grow on the medium provides for the identification of cells that have eliminated or evicted the selectable marker genes. An example is CodA (*Escherichia coli* cytosine deaminase), whose gene product deaminates 5-fluorocytosine (which is normally non-toxic as cells do not metabolize cytosine) to the toxic 5-fluorouracil.

Other negative selectable markers include the haloalkane dehalogenase (dhlA) gene of *Xanthobacter autotrophicus* GJ10 which encodes a dehalogenase, which hydrolyzes dihaloalkanes, such as 1,2-dichloroethane (DCE), to a halogenated alcohol and an inorganic halide (Naested et al., 1999, Plant J. 18(5):571-6).

The nucleic acid construct of the present invention is used to transform cells. The cells may be any type of cells including for example, mammalian cells, plant cells, yeast cells, fungal cells and insect cells. In one embodiment, the cells are transformed cells (i.e. part of a cell line). In another embodiment, the cells are isolated cells (i.e. removed from their source organism). In a particular embodiment, the isolated cells are cultured in suspension. According to a particular embodiment, the cells are plant cells and are optionally cultured in suspension.

Plant cells of the present invention are derived from a plant (or part thereof), preferably an edible and/or non toxic plant, which is amenable to genetic modification so as to bring about expression from the nucleic acid construct.

Examples of plants which may be used in accordance with this aspect of the present invention include, but are not limited to, moss, algae, monocot or dicot, as well as other plants. Examples include, but are not limited to, leafy crops, oil crops, alfalfa, tobacco, tomatoes, bananas, carrots, lettuce, maize, cucumber, melon, potatoes, grapes and white clover.

The plant cell may optionally be any type of plant cell such as a plant root cell (i.e. a cell derived from, obtained from, or originally based upon, a plant root), more preferably a plant root cell selected from the group consisting of, a celery cell, a ginger cell, a horseradish cell and a carrot cell.

According to a specific embodiment, the plant cells are carrot cells.

According to a specific embodiment, the plant cells are tobacco cells. According to a specific embodiment, the plant tobacco cells are BY-2 cells or *Nicotiana Benthamiana* cells.

Plant cells may be transformed stably or transiently with the nucleic acid constructs of some embodiments. In stable transformation, the nucleic acid molecule of some embodiments is integrated into the plant genome and as such it represents a stable and inherited trait. In transient transformation, the nucleic acid molecule is expressed by the cell transformed but it is not integrated into the genome and as such it represents a transient trait.

According to a specific embodiment, a plant or plant cell is stably transformed so as to express silencing agents (CRISPR components) to both XylT and FucT genes.

There are various methods of introducing foreign genes into both monocotyledonous and dicotyledonous plants (Potrykus, L, Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

It will be appreciated that the cells (which comprise the nucleic acid of the present invention) may have been further genetically modified to express a protein of interest. According to some embodiments, the polypeptide-of-interest is a pharmaceutical.

Alternatively or additionally, the polypeptide-of-interest is a human polypeptide.

Typically, the polypeptide of interest is a heterologous polypeptide. Heterologous glycoproteins, i.e. glycoproteins which are not normally expressed in plant cells in nature, may include mammalian or human proteins, which can be used as therapeutics such as e.g. monoclonal antibodies, enzymes etc. Conveniently, the foreign glycoproteins may be expressed from chimeric genes comprising a plant-expressible promoter and the coding region of the glycoprotein of interest, whereby the chimeric gene is transiently expressed or stably integrated in the genome of the plant cell. Methods of gene expression in plant cells are described hereinabove.

By "heterologous protein" it is understood a protein (i.e. a polypeptide) that is not expressed by the plant or plant cells in nature. This is in contrast with a homologous protein which is a protein naturally expressed by a plant or plant cell. Heterologous and homologous polypeptides that undergo post-translational N-glycosylation are referred to herein as heterologous or homologous glycoproteins.

Examples of polypeptides of interest that can be advantageously produced by the methods of this invention include, without limitation, cytokines, cytokine receptors, growth factors (e.g. EGF, HER-2, FGF-alpha, FGF-beta, TGF-alpha, TGF-beta, PDGF, IGF-I, IGF-2, NGF), growth factor receptors. Other examples include growth hormones (e.g. human growth hormone, bovine growth hormone); insulin (e.g., insulin A chain and insulin B chain), pro-insulin, erythropoietin (EPO), colony stimulating factors (e.g. G-CSF, GM-CSF, M-CSF); interleukins; vascular endothelial growth factor (VEGF) and its receptor (VEGF-R), interferons, tumor necrosis factor and its receptors, thrombopoietin (TPO), thrombin, brain natriuretic peptide (BNP); clotting factors (e.g. Factor VIII, Factor IX, von Willebrands factor and the like), anti-clotting factors; tissue plasminogen activator (TPA), urokinase, follicle stimulating hormone (FSH), luteinizing hormone (LH), calcitonin, CD proteins (e.g., CD2, CD3, CD4, CD5, CD7, CD8, CDI Ia, CDI Ib, CD18, CD19, CD20, CD25, CD33, CD44, CD45, CD71, etc.), CTLA proteins (e.g. CTLA4); T-cell and B-cell receptor proteins, bone morphogenic proteins (BNPs, e.g. BMP-I, BMP-2, BMP-3, etc.), neurotrophic factors, e.g. bone derived neurotrophic factor (BDNF), neurotrophins, e.g. rennin, rheumatoid factor, RANTES, albumin, relaxin, macrophage inhibitory protein (e.g. MIP-I, MIP-2), viral proteins or antigens, surface membrane proteins, ion channel proteins, enzymes, regulatory proteins, immunomodulatory proteins, (e.g. HLA, MHC, the B7 family), homing receptors, transport proteins, superoxide dismutase (SOD), G-protein coupled receptor proteins (GPCRs), neuromodulatory proteins, Alzheimer's Disease associated proteins and peptides. Fusion proteins and polypeptides, chimeric proteins and polypeptides, as well as fragments or portions, or mutants, variants, or analogs of any of the aforementioned proteins and polypeptides are also included among the suitable proteins, polypeptides and peptides that can be produced by the methods of the present invention. The protein of interest can be a glycoprotein. One class of glycoproteins are viral glycoproteins, in particular subunits, that can be used to produce for example a vaccine. Some examples of viral proteins comprise proteins from rhinovirus, poliomyelitis virus, herpes virus, bovine herpes virus, influenza virus, newcastle disease virus, respiratory syncitio virus, measles virus, retrovirus, such as human immunodeficiency virus or a parvovirus or a papovavirus, rotavirus or a coronavirus, such as transmissable gastroenteritis virus or a flavivirus, such as tick-borne encephalitis virus or yellow fever virus, a togavirus, such as rubella virus or eastern-, western-, or venezuelean equine encephalomyelitis virus, a hepatitis causing virus, such as hepatitis A or hepatitis B virus, a pestivirus, such as hog cholera virus or a rhabdovirus, such as rabies virus.

The heterologous glycoprotein can be an antibody or a fragment thereof. The term "antibody" refers to recombinant antibodies (for example of the classes IgD, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprise any modified or derivatised variants thereof that retain the ability to specifically bind an epitope. Antibody derivatives may comprise a protein or chemical moiety conjugated to an antibody. A monoclonal antibody is capable of selectively binding to a target antigen or epitope. Antibodies include, monoclonal antibodies (mAbs), humanized or chimeric antibodies, camelized antibodies, camelid antibodies (Nanobodies®), single chain antibodies (scFvs), Fab fragments, F(ab')$_2$ fragments, disulfide-linked Fvs (sdFv) fragments, anti-idiotypic (anti-Id) antibodies, intra-bodies, synthetic antibodies, and epitope-binding fragments of any of the above. The term "antibody" also refers to fusion protein that includes a region equivalent to the Fc region of an immunoglobulin. Also envisaged is the production in the plant or plant cells of the invention of so called dual-specificity antibodies (Bostrom J et al (2009) Science 323, 1610-1614).

Antibodies within the scope of the present invention include those comprising the amino acid sequences of the following antibodies: anti-TNFalpha antibodies such as Adalimumab (Humira™), anti-HER2 antibodies including antibodies comprising the heavy and light chain variable regions (see U.S. Pat. No. 5,725,856) or Trastuzumab such as HERCEPTIN™; anti-CD20 antibodies such as chimeric anti-CD20 as in U.S. Pat. No. 5,736,137, a chimeric or humanized variant of the 2H7 antibody as in U.S. Pat. No. 5,721,108; anti-VEGF antibodies including humanized and/or affinity matured anti-VEGF antibodies such as the humanized anti-VEGF antibody huA4.6.1 AVASTIN™ (WO 96/30046 and WO 98/45331); anti-EGFR (chimerized or humanized antibody as in WO 96/40210); anti-CD3 antibodies such as OKT3 (U.S. Pat. No. 4,515,893); anti-CD25 or anti-tac antibodies such as CHI-621 (SIMULECT) and (ZENAPAX) (U.S. Pat. No. 5,693,762). The present invention provides a method for the production of an antibody which comprises culturing a transformed plant cell or growing a transformed plant of the present invention. The produced antibody may be purified and formulated in accordance with standard procedures.

According to a specific embodiment, the polypeptide of interest is an enzyme.

According to a specific embodiment, the enzyme is a lysosomal enzyme. Examples include, but are not limited to, a cermidase e.g., N-acetylgalactosamine-4-sulphatase (arylsulphatase B), α-glucocerebrosidase, α-L-iduronidase, alpha-galactosidase A, beta-galactosidase.

The present invention provides a method for the production of a polypeptide of interest (e.g., lysosomal enzyme), which comprises culturing or growing a cell which has been transformed with the nucleic acid of the present invention and further transformed to express the polypeptide of interest. The produced polypeptide may be purified and formulated in accordance with standard procedures.

According to a specific embodiment the polypeptide of interest is a chimeric polypeptide e.g., the polypeptide f interest-attached to a heterologous polypeptide, also referred to as a fusion protein. Examples include but are not limited to Etanercept (Enbrel™), a chimeric polypeptide that fuses the TNF receptor to the constant end of the IgG1 antibody.

As mentioned, the removable, silencing construct described herein is used to initially silence a gene of interest after which it (or a part thereof) is excised.

Thus, according to another aspect of the present invention there is provided a method of editing or regulating a nucleic acid target of interest in an organism or cell thereof comprising:
(a) transforming the organism (e.g. plant) or isolated cells thereof (e.g. plant cells) with the nucleic acid construct described herein under conditions that promote editing or regulating of said nucleic acid of interest, wherein said conditions do not promote expression from said second promoter, and subsequently
(b) culturing said organism or isolated cells thereof under conditions so as to promote expression from said second promoter, thereby editing or regulating the nucleic acid target of interest.

In one embodiment, the transformation step comprises a stable transformation. In another embodiment, the transformation step comprises a transient transformation step. Following the transformation step of claim (a), the cells may be cultured for at least 6 hours, 12 hours, 1 day, two days, three days, four days, five days, six days, seven days, eight days, nine days, ten days, at least two weeks or at least three weeks.

The time of culturing typically depends on the cell type being transformed and whether the transformation is stable or transient.

Thus, for example in the case of plant cells, typically the cells are cultured for more than one week, more than two weeks—e.g. between 2 weeks-4 weeks following a stable transformation. Typically, plant cells are cultured for 1-7 days (e.g. between 1-3 days) following transient transformation.

The cells may be cultured in a positive selection medium during or following step (a) and prior to step (b), in order to identify cells that have been successfully transformed.

As used herein, the phrase "positive selective medium" refers to the medium or growth conditions which select for cells which contain a positive selectable marker gene. Transformed cells survive and/or grow when exposed to agents or conditions which would, normally, be detrimental to the survival of a cell that did not contain the positive selectable marker gene.

If the nucleic acid agent is a silencing agent, additional analyses may be carried out to confirm down-regulation of expression of the gene of interest (as further described herein above).

Next, the conditions are altered (or sufficient time is waited) such that they promote expression from the second promoter. The particular promoter will dictate what conditions are necessary (or how long is necessary) to promote expression therefrom. For example, if the promoter is a heat sensitive promoter, the temperature may be raised during this phase. If the promoter is a promoter only active in the flowering stage, sufficient time is waited to reach this developmental stage.

In step (b), the cells are cultured for at least three days, four days, five days, six days, seven days, eight days, nine days, ten days or even at least two weeks.

In order to select for cells that have lost the transgene, the cells may be cultured in a negative selection medium during or following step (b).

"Negative selective medium" describes medium or growth conditions which select for cells which do not contain a negative selectable marker gene. Transformed cells survive and/or grow when exposed to agents or conditions which would, normally, be detrimental to the survival of a cell which contained the negative selectable marker gene.

Additional analyses may be carried out to confirm the loss of the transgene (e.g. PCR analysis, Southern blot analysis etc.).

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, C I (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND METHODS

Plant Cell Suspensions

Nicotana tabacum cv. BY-2 cells (Nagata, 2004) were cultured as a suspension culture in liquid MS-BY-2 medium (Nagata and Kumagai, 1999) at 25° C. with constant agitation on an orbital shaker (85 r.p.m.). The suspensions were grown at 50 mL of volume in 250 mL Erlenmeyers and were sub-cultured weekly at 2.5% (v/v) concentration.

Construction of the Self-Removed Binary Vector

To construct the self-removed binary vector (FIG. 1), the pBIN19 backbone containing the human codon optimized Cas9 cassette and five cassettes of U6-gRNA directed to the FUC-T and XYL-T genes (described earlier, Hanania et al., 2017) was used. The T-DNA was bounded (downstream to the LB and upstream to the RB) by three repeats of Z sequence that were commercially synthesized by Genscript and contained three additional cassettes. The first cassette contained a Hygromycin phosphotransferase gene placed downstream of the nopaline synthase promoter and upstream of the nopaline synthase terminator, used for selection of transformed lines.

The second cassette contained a codA gene placed downstream of the 35s promoter and upstream of the octopine synthase terminator, used for selection of the self-removed clones. The third cassette, containing the gRNA-Z that was commercially synthesized by Genscript and placed downstream of the 18.2 Arabidopsis heat shock promoter and upstream of the octopine synthase terminator, was used to induce the T-DNA excision.

Transformation of BY-2 Cells and Selection of Lines

The final vector was used to transform the tobacco BY-2 cells via the *Agrobacterium* plant transformation procedure (An, 1985). Once a stable transgenic cell suspension was established, it was used for isolating and screening individual cell lines (clones).

Establishing of individual cell lines was conducted by using highly diluted aliquots of the transgenic cell suspension and spreading them on solid medium. The cells were allowed to grow until small calli (plant cell mass) developed. Each callus, representing a single clone, was then re-suspended in liquid medium and sampled.

Screening of the XylT FucT Knocked-Out Lines and Testing the Re-Clone Lines from Pool 76

Individual transformed lines were screened using an ELISA test for the absence of Fucose and Xylose containing glycans as described previously (Hanania et al., 2017). Lines (28, 76, 90) that were assumed to be knocked out for the FucT or XylT genes at the first screening stage, were then analyzed by SDS-PAGE and Western blot using anti-HRP antibodies (Agrisera ASO9-549). For further analysis, anti-Cas9 (Millipore MAC133) and anti-codA antibodies (custom prepared by Genscript) were used. Eight clones from 76-pool were then analyzed by Western blot using anti-Cas9 (Millipore MAC133) and anti-codA (custom prepared by Genscript) and anti-hptII antibodies (Artron Bio research Inc. A85-Abl).

Total Protein Extraction

A total of 100 mg of cells were transferred into 2 ml tube containing one glass bead (5 mm). A volume of 200 μl sample buffer (100 mM Tris HCL buffer pH 6.8, 4% SDS, 0.5 M DTT, 30% glycerol and 0.4 mg/ml of bromophenol blue) were added and the sample was tissue-lysed for 10 minutes at 28 Hz. The sample was boiled for 10 min. and centrifuged at 20,000 g for 10 min. and supernatant was transferred into a new tube.

PCR Reactions

PCR was performed using forward and reverse primers with 35 cycles of the following procedure: 95° C. for 1 minute, 60° C. for 20 sec. and 72° C. for 1 min. The PCR products were separated by electrophoresis on an ethidium bromide-stained 1% agarose gel.

Heat Induction and Selection on Medium Supplemented with 5-FC

To induce the expression of the sgRNA-ZZZ in the XylT/FucT knockout BY-2 cell lines 28, 76 & 90, the cultures were repeatedly (twice weekly for 2 consecutive week) exposed to heat treatment (2.5 hours 37° C.) in a water bath. After induction and for the selection of cells in which the transgene was excised, the cells were transferred to selection medium containing 750 mg/L 5-FC while the Hygromycin (that served as a selection agent in the previous step) was omitted.

Analysis of Genome Modifications of the Knocked-Out Cell Lines

Genomic DNA was extracted using the DNeasy plant mini kit (Qiagen). The DNA was amplified by PCR using specific primers for XylT and FucT genes (Table 1).

TABLE 1

Primers used for identification and characterization of the mutations in the knocked out cell lines.

| # | Name | Sequence |
|---|---|---|
| 1 | For-XylT(A, B) | 5' CTCTTCGCTCTCAACTCAATCACTCT C 3'<br>SEQ ID NO: 1 |
| 2 | Rev-XylT(A, B) | 5' ATTAAYTCACGCATAGTGTGCCTTGA AAT 3'<br>SEQ ID NO: 2 |
| 3 | For-FucT(A, B, C) | 5' GAAGGTGTTGGGTCATCATCACCTAC AAA 3'<br>SEQ ID NO: 3 |
| 4 | Rev-FucT(A, B, C) | 5' TTCTAGATGTGCTTACCCACCGTCGT GC 3'<br>SEQ ID NO: 4 |
| 5 | For-FucT(D, E) | 5' GGTTAGTGCTCTTCGTTACATTGAGT CAC 3'<br>SEQ ID NO: 5 |
| 6 | Rev-FucT(D, E) | 5' CATCCAGAAAGATGATTTGTCCACAA CATT 3'<br>SEQ ID NO: 6 |

(1, 2)-set of primers designed to produce XylT (A and B) alleles. (3, 4)-set of primers designed to produce FucT (A, B and C) alleles. (5, 6)-set of primers designed to produce FucT (D and E) alleles. For-forwards; Rev-reverse.

The PCR products were sub-cloned into the pGEMT vector. Colonies were sequenced and were aligned with the wild-type target sequences to determine the mutations.

Southern Blot Analysis

Total genomic DNA for southern blot analysis was isolated from BY-2 cells based on (Shure et al., 1983) with additional steps, as detailed below.

Ten grams of BY2 cells harvested at day 5 were grounded in liquid nitrogen with mortar and pestle. The powdered cells were transferred into 100 ml lysis buffer containing 8 M urea, 0.35 M NaCl, 0.05 M Tris-HCl (pH 7.5), 0.02 M EDTA, 2% Sarcosyl, 0.3% Sodium thiosulfate and 1% PVP-40. The mixture was incubated in a 70° C. hot water bath for 60 min. An equal amount of mixed Phenol-Chloroform-Isoamilalcohol (25:24:1) was added, mixed and the phases were separated by centrifugation. Phenol-chloroform extraction was repeated twice. The DNA was sediment after addition of an equal amount of cold Isopropanol, washed with 80% ethanol, dried and immediately dissolved in 1.5 ml TE buffer containing 25 μl of RNaseA (10 μg/ml) and incubated at RT for overnight. An equal amount of mixed Phenol-Chloroform-Isoamilalcohol (25:24:1) was added, mixed and the phases were separated by centrifugation. Chloroform extraction was repeated twice. The phases were separated and an equal amount of Isopropanol was added to the upper phase and centrifuged. Pellet was sediment, washed with 80% ethanol, dried and re-suspended with 400 ul TE.

Digested DNA was then separated on 0.8% agarose gel electrophoresis system at 100 V for 5 hours in 1×TAE.

Separated DNA was then capillary transferred to a nylon membrane and immobilized by UV-crosslinking using Stratalinker (Stratagene). Hybridization was done using DIG probes. Signal intensity was scanned with high resolution chemiluminescence settings using a ChemiDoc Touch Imaging System (Bio Rad) with Image Lab™ Software ver 5.2.1 (Bio Rad).

Results

Construction of the 'Self-Removable' CRISPR-Cas9 Vector

Figure 1:
FIG. 1: Schematic description of the 'self-removable' CRISPR-Cas9 vector used for the transformation of the BY-2 cells.

To enable its own self-excision and the subsequent selection of 'transgene-free' cell lines thereafter, the construct described in Hanania et al., 2017 (which was designed to drive the constitutive expression of Cas9 together with five sets of gRNAs targeted to the N. tabacum xylosyltransferase and fucosyltransferase (XylT/FucT) genes) was further supplemented with the following components: (1) three repeats of 23 nucleotides each, designated as "ZZZ", which were framed on its two edges; (2) an additional g-RNA-Z driven by the heat inducible HSP18.2 promoter (Takahashi and Komeda, 1989); and (3) a cytosine deaminase (codA) negative selectable marker (de Oliveira et al., 2015) driven by a 35S promoter (FIG. 1, Table 2).

TABLE 2 sequences of the cas9 target and g-RNA for excision

| Name | Sequence |
|---|---|
| Z | 5' GCGCTTCAAGGTGCGCATGGAGG 3'<br>SEQ ID NO: 7 |
| ZZZ | 5' GCGCTTCAAGGTGCGCATGGAGGTTAGGCGCGCTTCAAGG<br>TGCGCATGGAGGGGCGCGCGCTTCAAGGTGCGCATGG 3'<br>SEQ ID NO: 8 |
| gRNA-Z | 5' GCGCTTCAAGGTGCGCATGG 3'<br>SEQ ID NO: 9 |

Three repeats of the Z sequence (ZZZ) were constructed at both boundaries of the 'self-removable' vector. An inducible gRNA-Z was included in the vector and once heat shock induced and transcribed, was used to target the Cas9 to the two ZZZ sites at both sides of the integrated insert (T-DNA).

The three 23 nucleotides repeats, which do not exist on the N. tabacum genome, were designed to serve as targets for the Cas9-gRNA-Z. The heat inducible promoter was used to allow for sequential targeting control of the Cas9 activity and the codA was used to enable the selection of 'transgene-free' cell lines.

Using the above described 'self-removable' vector, the Cas9 activity on different targets can be sequentially controlled. At first, Cas9 is guided, by the constitutively expressed gRNAs-XylT/FucT to knockout the two plant glycotransferases, xylosyl transferanse and fucosyl transferase. Once the knockout is accomplished and confirmed, a second step is triggered by heat induction in order to express the gRNA-Z, subsequently targeting the Cas9 to the two ZZZ borders. Dual, simultaneous, DNA digestions, at both sides of the transgenic insert, can result in the excision of the entire DNA insert from the cell genome, followed by non-homologous end joining (NHEJ) DNA repair (Gorbunova and Levy, 1997; Gorbunova and Levy, 1999). This chain of events can consequently result in XylT/FucT knockout cells which are free from foreign DNA.

Knockout of the XylT and FucT Genes Using the 'Self-Removable' CRISPR-Cas9 Vector The above described vector was used to stably transform N.tabacum BY-2 cells. A total of 100 transformed clones (selected on Hygromycin) were isolated. To select for Xylose/Fucose free clones these lines were subjected to an ELISA test. Three cell lines 28, 76 and 90 out of the 100 tested clones, presented a putative knockout of both XylT/FucT genes (ΔXF). Further analysis by Western blot confirmed that these 3 clones were not detected by the anti-HRP antibodies and are fully devoid of glycans containing Xylose and Fucose (FIG. 2).

In order to activate the self-excision step and to enable the selection of cells that lost the transgene, the presence of the codA and the Cas9 in lines 28, 76 and 90 was essential. To confirm the expression of codA and Cas9 genes in these three selected cell lines, further analysis was done by Western blot using anti-codA and anti-Cas9 antibodies. All three lines exhibited codA expression, though at significantly different levels (FIG. 3). Cas9 expression in line 28 was relatively high, while line 76 presented a lower expression level and line 90 did not show any signal of Cas9 (FIG. 4). As Cas9 was not detected in line 90, this cell line was omitted at this point.

Activating the 'Se-Removable' Mechanism for the Excision of the Inserted T-DNA

Once the targeted mutations of the XylT and FucT genes were accomplished and confirmed, the self-removal mechanism was activated by inducing the expression of the gRNA-Z. The two selected cell lines (lines 28 and 76) were repeatedly heat treated, followed by cultivation in 5-Flurocytosine (5-PC) supplemented culture medium. The presence of the 5-PC in the culture medium served to select for the cell population, which lost the codA activity (cells expressing codA do not survive in the present of 5-FC). Cells that survived the 5-FC medium, were assumed to have lost the codA coding sequence, either by partial deletion or by excision of the entire recombinant DNA insert(s). Assuming that the cas9:gRNA-Z activity resulted in a heterogenic cell population, the post induced cells were labeled as 28-pool and 76-pool, hereafter.

Assessing Likelihood for Excision Events and Selecting a Cell Pool for Further Analysis In order to detect functionality of Cas9:gRNA-Z complex, on the ZZZ target, and to assess the probability of occurrence of potential excision events, the 28-pool and 76-pool cells were subjected to PCR analysis using forward primer for the left border of the T-DNA and reverse primer for the hptII gene, outside the boundaries of left ZZZ sequence (FIGS. 5A-B; Table 3—primers 1, 2). It should be noted that the PCR products were generated from a heterogenic pool of cells, thus some products may have been missed by the PCR.

TABLE 3

Primers used to detect excision activity.

| # | Name | Sequence |
|---|---|---|
| 1 | For-LB | 5' CAGGATATATTGTGGTGTAAACAAATTGACGC 3'<br>SEQ ID NO: 10 |
| 2 | Rev-hptII | 5' GACCGGCTGAAGAACAGCGGGCAGTTCGGTTT<br>C 3'<br>SEQ ID NO: 11 |
| 3 | Rev-RB | 5' CAAACACTGATAGTTTAAACTGAAGGCGGG 3'<br>SEQ ID NO: 12 |

TABLE 3-continued

Primers used to detect excision activity.

| # | Name | Sequence |
|---|------|----------|
| 4 | For-HSP | 5' CTTTCCATGGTCATTTCTTCTGGTTCAAG 3'<br>SEQ ID NO: 13 |
| 5 | Rev-HSP | 5' CCTCTTCGAGATACGGGCTCAGTG 3'<br>SEQ ID NO: 14 |

Primers 1,2—set of primers (FIGS. 5A-B) targeted at the left border of the vector and produce a 874 bp DNA fragment (in case of non-excision). PCR failure to produce this fragment can indicate mutations within the left ZZZ sequence. Primers 1, 3—set of primers used to amplify the surplus fragment left between the left and right borders after excision. Primers 4,5—set of primers (FIG. 7) to test for the present of the heat shock promoter sequence in the cells grew after induction and 5-FC selection. For—forwards; Rev—reverse.

A fragment of 874 bp (FIG. 5A) is expected to be produced in cells that did not undergo Cas9:gRNA-Z activity. PCR failure to produce this fragment or any PCR product other than the predicted 874 bp size can indicate endonuclease activity within the left ZZZ repeat sequence.

Using the above described forward and reverse primers, a ~600 bp fragment was produced with the 28-pool cells and no PCR product was detected in the 76-pool cells (FIG. 5B). These results can indicate the occurrence of some mutations within the left ZZZ sequence of the 28-pool and the loss of this sequence within the 76-pool, serving as evidence for the actual functionality of the Cas9:gRNA-Z. The 76-pool was chosen for further analyses, since it demonstrated the highest likelihood for an excision event(s) to occur.

Cloning of the 76-Pool and Characterization of the Isolated Clones

The cells of the 76-pool that were selected on 5-FC were plated on solid medium and 8 clones (761-768) were raised and analyzed by Western blot analysis. All these clones were negative to anti-hptII, anti-Cas9 and anti-codA antibodies (FIGS. 6A-C). Moreover, these lines could not grow in the presence of Hygromycin.

The above selected clones were further analyzed, by PCR, for the presence of the heat shock promoter (HSP1&2) sequence. Four clones 763, 766, 767 and 768 were found negative for HSP18.2, while a PCR product was obtained in the other four 76-pool originated clones (FIG. 7; Table 3—primers 4, 5). Two clones (763 and 767) were chosen for further characterization studies.

Confirming Complete Excision by Southern Blot Analysis

Complete excision and the absence of the entire T-DNA in the genome of lines 763 and 767 were determined by Southern-blot analysis using 4 different probes covering the entire T-DNA at ten different locations. To confirm the absence of a 3.8 kb section at the 5' of the T-DNA, genomic DNA was digested with PacI and sacI restriction enzymes and the membrane was hybridized with a DIG hptII probe. No signal was detected in these lines (FIGS. 8A-B). To confirm the absence of a 9 kb section downstream to hptII gene, genomic DNA was digested with a single NcoI restriction enzyme and the membrane was hybridized with a DIG hCas9 probe. No signal was detected in these lines (FIGS. 9A-B). To confirm the absence of a 12.4 kb section downstream to hptII gene, genomic DNA was digested with NcoI and SphI restriction enzymes and the membrane was hybridized with a DIG OcST probe. No signal was detected in these lines (FIGS. 10A-B). To confirm the absence of the five cassettes of U6-gRNA, genomic DNA was digested with SacI and PacI restriction enzymes and the membrane was hybridized with a DIG U6-gRNA probe. No signal was detected in these lines (FIGS. 11A-B).

While using primers to the left and to the right borders (Table 3 primers 1,3) of the inserted T-DNA (nearby the ZZZ sequences), aiming at characterization of the precise sites of the excision, no PCR product was detected. This could be explained by the occurrence of occasional deletions around the break sites. Consequently, it could not be determined whether a few bases from the borders of the T-DNA were left at the excision sites.

Characterization of the Mutations Generated by the Cas9 Multiplexed Targeting of the XylT and the FucT Genes Cell line 763 was further characterized for the Cas9 generated mutations of the XylT and the FucT genes. A PCR was performed using 3 sets of primers (Table 3) flanking the Cas9 target sites of XylT (A and B genes), FucT (A, B and C genes) and FucT (D and E genes), respectively. The obtained PCR products were cloned into a pGEMT vector and the sub-clones from each sample were sequenced, revealing the presence of assorted insertions and/or deletions (in-dels). No wild type products were detected among any of the tested genes.

Three mutations for the XylT genes and seven mutations for the FucT genes were identified. An identical 7 bp deletion was found in both alleles of the XylT-A gene. A 18 bp deletion and a 7 bp deletions where identified in the XylT-B gene. An identical 1,218 bp deletion and 1 bp insertion was found in both alleles of the FucT-A gene. A 16 bp deletion in one allele and a 17 bp deletion and 1 bp insertion in the other were found in FucT-B. A 1 bp deletion and 1 bp insertion in one allele and 1 bp deletion and 1 bp insertion in the other were found in FucT-C.

An identical 1,376 bp deletion and 395 bp insertion was found in both alleles of the FucT-D gene and an identical 16 bp deletion and 53 bp insertion was found in both alleles of the FucT-E gene.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

REFERENCES

An G (1985) High efficiency transformation of cultured tobacco cells. *Plant physiology* 79:568-570.

Cai Y, Chen L, Sun S, Wu C, Yao W, Jiang B, Han T and Hou W (2018) CRISPR/Cas9-Mediated Deletion of Large Genomic Fragments in Soybean. *International journal of molecular sciences* 19:3835.

Char S N, Neelakandan A K, Nahampun H, Frame B, Main M, Spalding M H, Becraft P W, Meyers B C, Walbot V, Wang K and Yang B (2017) An *Agrobacterium*-delivered CRISPR/Cas9 system for high-frequency targeted mutagenesis in maize. *Plant Biotechnology Journal* 15:257-268.

Chen L, Li W, Katin-Grazzini L, Ding J, Gu X, Li Y, Gu T, Wang R, Lin X, Deng Z, McAvoy R J, Gmitter F G, Deng Z, Zhao Y and Li Y (2018) A method for the production and expedient screening of CRISPR/Cas9-mediated non-transgenic mutant plants. *Horticulture Research* 5:13.

Chong-Perez B, Kosky R G, Reyes M, Rojas L, Ocana B, Tejeda M, Perez B and Angenon G (2012) Heat shock induced excision of selectable marker genes in transgenic banana by the Cre-lox site-specific recombination system. *Journal of Biotechnology* 159:265-273.

Cuellar W, Gaudin Al, Solorzano D, Casas Mollano J, Nopo-Olazabal L, Chudalayandi P, Medrano G, Kreuze J and Ghislain M (2006) *Self-excision of the antibiotic resistance gene nptII using a heat inducible Cre-loxP system from transgenic potato.*

Dahan-Meir T, Filler-Hayut S, Melamed-Bessudo C, Bocobza S, Czosnek H, Aharoni A and Levy A A (2018) Efficient in planta gene targeting in tomato using geminiviral replicons and the CRISPR/Cas9 system. The Plant Journal 95:5-16.

Dale E C and Ow D W (1991) Gene transfer with subsequent removal of the selection gene from the host genome. *Proceedings of the National Academy of Sciences of the United States of America* 88:10558-10562.

de Oliveira M L P, Stover E and Thomson J G (2015) The codA gene as a negative selection marker in Citrus. *SpringerPlus* 4:264.

Filler Hayut S, Melamed Bessudo C and Levy A A (2016) Targeted recombination between homologous chromosomes for precise breeding in tomato. *Nature Communications* 8:15605.

Gao X, Chen J, Dai X, Zhang D and Zhao Y (2016) An Effective Strategy for Reliably Isolating Heritable and Cas9 Free *Arabidopsis* Mutants Generated by CRISPR/Cas9-Mediated Genome Editing. *Plant Physiology* 171:1794-1800.

Gorbunova V and Levy A A (1997) Non-homologous DNA end joining in plant cells is associated with deletions and filler DNA insertions. *Nucleic Acids Research* 25:4650-4657.

Gorbunova V and Levy A A (1999) How plants make ends meet: DNA double-strand break repair. *Trends in Plant Science* 4:263-269.

Hanania U, Ariel T, Tekoah Y, Fux L, Sheva M, Gubbay Y, Weiss M, Oz D, Azulay Y, Turbovski A, Forster Y and Shaaltiel Y (2017) Establishment of a tobacco BY2 cell line devoid of plant-specific xylose and fucose as a platform for the production of biotherapeutic proteins. *Plant Biotechnology Journal* 15:1120-1129.

Hao H, Wang X, Jia H, Yu M, Zhang X, Tang H and Zhang L (2016) Large fragment deletion using a CRISPR/Cas9 system in *Saccharomyces cerevisiae*. *Analytical Biochemistry* 509:118-123.

Hare P D and Chua N-H (2002) Excision of selectable marker genes from transgenic plants. *Nature Biotechnology* 20:575.

He Y, Zhu M, Wang L, Wu J, Wang Q, Wang R and Zhao Y (2018) Programmed Self-Elimination of the CRISPR/Cas9 Construct Greatly Accelerates the Isolation of Edited and Transgene-Free Rice Plants. *Molecular Plant* 11:1210-1213.

He Z, Proudfoot C, Mileham A J, McLaren D G, Whitelaw C B A and Lillico S G (2014) Highly efficient targeted chromosome deletions using CRISPR/Cas9. *Biotechnology and Bioengineering* 112:1060-1064.

Jansing J, Sack M, Augustine S M, Fischer R and Bortesi L (2019) CRISPR/Cas9-mediated knockout of six glycosyltransferase genes in *Nicotiana benthamiana* for the production of recombinant proteins lacking $^2$-1,2$^-$-xylose and core 1,3-±$^-$-fucose. *Plant biotechnology journal* 17:350-361.

Khattri A, Nandy S and Srivastava V (2011) *Heat-inducible Cre-lox system for marker excision in transgenic rice.*

Komari T, Hiei Y, Saito Y, Murai N and Kumashiro T (1996) Vectors carrying two separate T-DNAs for co-transformation of higher plants mediated by *Agrobacterium tumefaciens* and segregation of transformants free from selection markers. *The Plant Journal* 10:165-174.

Koonin E V, Makarova K S and Zhang F (2017) Diversity, classification and evolution of CRISPR-Cas systems. *Current Opinion in Microbiology* 37:67-78.

Kumlehn J, Pietralla J, Hensel G, Pacher M and Puchta H (2018) The CRISPR/Cas revolution continues: From efficient gene editing for crop breeding to plant synthetic biology. *Journal of Integrative Plant Biology* 60:1127-1153.

Li R, Char S N and Yang B (2019) Creating Large Chromosomal Deletions in Rice Using CRISPR/Cas9, in *Plant Genome Editing with CRISPR Systems: Methods and Protocols* pp 47-61, New York, NY: Springer New York.

Liu J-J, Orlova N, Oakes B L, Ma E, Spinner H B, Baney KLM, Chuck J, Tan D, Knott G J, Harrington L B, Al-Shayeb B, Wagner A, Brltzmann J, Staahl B T, Taylor K L, Desmarais J, Nogales E and Doudna J A (2019) CasX enzymes comprise a distinct family of RNA-guided genome editors. *Nature* 566:218-223.

Lu H P, Liu S M, Xu S L, Chen W Y, Zhou X, Tan Y Y, Huang J Z and Shu Q Y (2017) CRISPR-S: an active interference element for a rapid and inexpensive selection of genome-edited, transgene-free rice plants. *Plant Biotechnology Journal* 15:1371-1373.

Ma X, Zhang Q, Zhu Q, Liu W, Chen Y, Qiu R, Wang B, Yang Z, Li H, Lin Y, Xie Y, Shen R, Chen S, Wang Z, Chen Y, Guo J, Chen L, Zhao X, Dong Z and Liu Y-G (2015) A Robust CRISPR/Cas9 System for Convenient, High-Efficiency Multiplex Genome Editing in Monocot and Dicot Plants. *Molecular Plant* 8:1274-1284.

Mercx Sb, Smargiasso N, Chaumont Fo, De Pauw E, Boutry M and Navarre C (2017) Inactivation of the 1,2)$^{2-}$)-xylosyltransferase and the 1,3)±$^-$)-fucosyltransferase genes in *Nicotiana tabacum* BY-2 Cells by a Multiplex CRISPR/Cas9 Strategy Results in Glycoproteins without Plant-Specific Glycans. *Frontiers in plant science* 8:403-403.

Nagata T (2004) When I Encountered Tobacco BY-2 Cells!, in *Tobacco BY-2 Cells* pp 1-6, Berlin, Heidelberg: Springer Berlin Heidelberg.

Nagata T and Kumagai F (1999) Plant cell biology through the window of highly sychronized tobacco BY-2 cell line.

Ordon J, Gantner J, Kemna J, Schwalgun L, Reschke M, Streubel J, Boch J and Stuttmann J (2017) Generation of chromosomal deletions in dicotyledonous plants employing a user-friendly genome editing toolkit. *The Plant Journal* 89:155-168.

Shan Q, Wang Y, Li J, Zhang Y, Chen K, Liang Z, Zhang K, Liu J, Xi J J, Qiu J-L and Gao C (2013) Targeted genome modification of crop plants using a CRISPR-Cas system. *Nature Biotechnology* 31:686.

Shure M, Wessler S and Fedoroff N (1983) Molecular identification and isolation of the Waxy locus in maize. *Cell* 35:225-233.

Takahashi T and Komeda Y (1989) Characterization of two genes encoding small heat-shock proteins in *Arabidopsis thaliana*. *Molecular and General Genetics MGG* 219: 365-372.

Wang Y, Chen B, Hu Y, Li J and Lin Z (2005) Inducible Excision of Selectable Marker Gene from Transgenic Plants by the Cre/lox Site-specific Recombination System. *Transgenic Research* 14:605-614.

Woo J W, Kim J, Kwon S I, Corvalán C, Cho S W, Kim H, Kim S-G, Kim S-T, Choe S and Kim J-S (2015) DNA-free genome editing in plants with preassembled CRISPR-Cas9 ribonucleoproteins. *Nature Biotechnology* 33:1162.

Xiao A, Wang Z, Hu Y, Wu Y, Luo Z, Yang Z, Zu Y, Li W, Huang P, Tong X, Zhu Z, Lin S and Zhang B (2013) Chromosomal deletions and inversions mediated by TAL-ENs and CRISPR/Cas in zebrafish. *Nucleic Acids Research* 41:e141-e141.

Yoder J I and Goldsbrough A P (1994) Transformation Systems for Generating Marker-Free Transgenic Plants. *Bio/Technology* 12:263.

Zhang H, Zhang J, Wei P. Zhang B, Gou F, Feng Z, Mao Y, Yang L, Zhang H, Xu N and Zhu J-K (2014) The CRISPR/Cas9 system produces specific and homozygous targeted gene editing in rice in one generation. *Plant Biotechnology Journal* 12:797-807.

Zhang L, Jia R, Palange N J, Satheka A C, Togo J, An Y, Humphrey M, Ban L, Ji Y, Jin H, Feng X and Zheng Y (2015) Large genomic fragment deletions and insertions in mouse using CRISPR/Cas9. *PloS one* 10:e0120396-e0120396.

Zhang W, S. Subbarao, P. Addae, A. Shen, C. Armstrong, V. Peschke and Gilbertson L (2003) Cre/lox-mediated marker gene excision in transgenic maize (*Zea mays* L.) plants. *Theoretical and Applied Genetics* 107:1157-1168.

Zhang Y, Liang Z, Zong Y, Wang Y, Liu J, Chen K, Qiu J-L and Gao C (2016) Efficient and transgene-free genome editing in wheat through transient expression of CRISPR/Cas9 DNA or RNA. *Nature Communications* 7:12617.

Zhou H, Liu B, Weeks D P, Spalding M H and Yang B (2014) Large chromosomal deletions and heritable small genetic changes induced by CRISPR/Cas9 in rice. *Nucleic Acids Research* 42:10903-10914.

What is claimed is:

1. A method of editing or regulating a nucleic acid target of interest in an organism or cell thereof comprising:
   (a) transforming the organism or isolated cells thereof with a nucleic acid construct which comprises a sequence which encodes:
   (i) at least one gRNA operatively linked to a constitutive promoter, wherein said gRNA is for editing or regulating at least one nucleic acid target of interest in said organism or cell of said organism;
   (ii) at least one construct-eliminating gRNA operatively linked to an inducible promoter;
   (iii) a CRISPR endonuclease operatively linked to a constitutive promoter; and
   (iv) at least two copies of a target sequence for said construct-eliminating gRNA, wherein a first of said at least two copies is positioned 3' to (i), (ii) and (iii) and a second of said at least two copies is positioned 5' to (i), (ii) and (iii),
   wherein said transforming is effected under conditions that promote editing or regulating of said nucleic acid of interest, wherein said conditions comprise culturing for at least three weeks, wherein said conditions do not promote expression from said inducible promoter; and subsequently
   (b) culturing said organism or isolated cells thereof under conditions so as to promote expression from said inducible promoter, thereby editing or regulating the nucleic acid target of interest.

2. The method of claim 1, wherein said nucleic construct further encodes:
   (v) a negative selectable marker; and
   (vi) a positive selectable marker, wherein a first of said at least two copies is positioned 3' to (i), (ii), (iii), (v) and (vi), and a second of said at least two copies is positioned 5' to (i), (ii), (iii), (v) and (vi).

3. The method of claim 1, wherein said at least two copies of a target sequence for said gRNA comprises at least six copies of said target sequence for said gRNA, wherein three of said at least six copies are positioned 3' to (i), (ii) and (iii) and another three of said at least six copies are positioned 5' to (i), (ii) and (iii).

4. The method of claim 1, wherein said nucleic acid target of interest is comprised in a gene.

5. The method of claim 4, wherein said gene encodes a glycosylating enzyme.

6. The method of claim 5, wherein said glycosylating enzyme comprises xylosyltransferase and/or fucosyltransferase.

7. The method of claim 1, wherein said organism is a plant.

8. The method of claim 1, wherein said at least one nucleic acid target of interest is a plurality of nucleic acid targets of interest.

* * * * *

```
                        SEQUENCE LISTING

<160> NUMBER OF SEQ ID NOS: 28

<210> SEQ ID NO 1
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 1
ctcttcgctc tcaactcaat cactctc                                        27

<210> SEQ ID NO 2
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 2
attaaytcac gcatagtgtg ccttgaaat                                      29

<210> SEQ ID NO 3
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 3
gaaggtgttg ggtcatcatc acctacaaa                                      29

<210> SEQ ID NO 4
<211> LENGTH: 28
<212> TYPE: DNA
<213> ORGANISM: Artificial sequence
<220> FEATURE:
```

<223> OTHER INFORMATION: Single strand DNA oligonucleotide

<400> SEQUENCE: 4
ttctagatgt gcttacccac cgtcgtgc                                28

<210> SEQ ID NO 5
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 5
ggttagtgct cttcgttaca ttgagtcac                               29

<210> SEQ ID NO 6
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 6
catccagaaa gatgatttgt ccacaacatt                              30

<210> SEQ ID NO 7
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 7
gcgcttcaag gtgcgcatgg agg                                     23

<210> SEQ ID NO 8
<211> LENGTH: 77
<212> TYPE: DNA
<213> ORGANISM: Artificial sequence
<220> FEATURE:
<223> OTHER INFORMATION: Single strand DNA oligonucleotide

<400> SEQUENCE: 8
gcgcttcaag gtgcgcatgg aggttaggcg cgcttcaagg tgcgcatgga ggggcgcgcg      60
cttcaaggtg cgcatgg                                            77

<210> SEQ ID NO 9
<211> LENGTH: 20
<212> TYPE: DNA
<213> ORGANISM: Artificial sequence
<220> FEATURE:
<223> OTHER INFORMATION: gRNA nucleic acid sequence

<400> SEQUENCE: 9
gcgcttcaag gtgcgcatgg                                         20

<210> SEQ ID NO 10
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 10
caggatatat tgtggtgtaa acaaattgac gc                           32

<210> SEQ ID NO 11
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 11
gaccggctga agaacagcgg gcagttcggt ttc                                    33

<210> SEQ ID NO 12
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 12
caaacactga tagtttaaac tgaaggcggg                                        30

<210> SEQ ID NO 13
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 13
ctttccatgg tcatttcttc tggttcaag                                         29

<210> SEQ ID NO 14
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 14
cctcttcgag atacgggctc agtg                                              24

<210> SEQ ID NO 15
<211> LENGTH: 5
<212> TYPE: DNA
<213> ORGANISM: Artificial sequence
<220> FEATURE:
<223> OTHER INFORMATION: protospacer adjacent motif amino acid sequence
<220> FEATURE:
<221> NAME/KEY: misc_feature
<222> LOCATION: (1)..(2)
<223> OTHER INFORMATION: n is a, c, g, or t

<400> SEQUENCE: 15 nngrr                                                                   5

<210> SEQ ID NO 16
<211> LENGTH: 8
<212> TYPE: DNA
<213> ORGANISM: Artificial sequence
<220> FEATURE:
<223> OTHER INFORMATION: protospacer adjacent motif amino acid sequence
<220> FEATURE:
<221> NAME/KEY: misc_feature
<222> LOCATION: (1)..(4)
<223> OTHER INFORMATION: n is a, c, g, or t

<400> SEQUENCE: 16 nnnngatt                                                                      8

<210> SEQ ID NO 17
<211> LENGTH: 8
<212> TYPE: DNA
<213> ORGANISM: Artificial sequence
<220> FEATURE:
<223> OTHER INFORMATION: protospacer adjacent motif amino acid sequence
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(8)
<223> OTHER INFORMATION: n is a, c, g, or t

<400> SEQUENCE: 17 nnnngnnn                                                                      8

<210> SEQ ID NO 18
<211> LENGTH: 2161
<212> TYPE: DNA
<213> ORGANISM: Artificial sequence
<220> FEATURE:
<223> OTHER INFORMATION: Sequence of the PCR produced fragment

<400> SEQUENCE: 18
atgaacaaga aaaagctgaa atttcttgtt tctctcttcg ctctcaactc aatcactctc      60
tatctctact tctcttccca ccctgatcac ttccgccaca aatcccgcca aaaccacttt     120
tccttgtcgg aaaaccgcca tcataatttc cactcttcaa tcacttctca atattccaag     180
ccttggccta ttttgccctc ctacctccct tggtctcaaa accctaatgt tgtttggaga     240
tcgtgcgagg gttacttcgg taatgggttt actctcaaag ttgaccttct caaaacttcg     300
ccggagtttc accggaaatt cggcgaaaac accgtctccg gcgacggcgg atggtttagg     360
tgttttttca gtgagacttt gcagagttcg atctgcgagg gaggcgcaat acgaatgaat     420
ccggacgaga ttttgatgtc tcgtggaggt gagaaattgg agtcggttat ggtaggagt      480 gaagatgatg agctgcccgt gttcaaaaat ggagcttttc agattaaagt tactgataaa     540
ctgaaaattg gaaaaaaatt agtggatgaa aaattcttga ataaatactt accggaaggt     600
gcaatttcaa ggcacactat gcgtgagtta attgactcta ttcagttggt tggcgccgat     660
gattttcact gttctgaggt tagattttga atttttgttt gctctttaaa ttaaaggttt     720
aaactttgtg aatgttggca gatatggaat acactaatgg attttgtttg atctgtttaa     780
tgaagattgt ctagaacctc aatgttataa atatggtttg gttgcttcat taattaaaga     840
gaattcctta atatcccgac tagatgccag ataacaccag ttagttgact tttggattat     900
tggttgcatt tcatttgatc agataaattg ttcattctta aatgtttcac taagaattta     960
ctcaagattt cagagtttat atgtaggtgt atgtatttgg aattctggat ttggatctag    1020
tattgaatgg attactgaac ttgtactccc cagtcatctg ggggaggagca atagatcaaa    1080 ttcaagggtt gaaaagtaat actgagtcag aaattaacca ctttaacttg gaaaacggta    1140
aatgtatgtg ttctaagatg gttattccta aacttttga tgtctaatat ggagaaagtg     1200
agttgattta tgcttttttcc ttttcccttt attggtgttg ttttttaaat tctatcaatt   1260
cctttgtttg attgctactc aaattgaacc ttagacggag tagcaatagc aaaaagtgaa    1320
ggccattctt ttctcctttc atctctttat ttccgtttga catacagaat atggtagcat    1380
ctgtctgaag tggttaattt tattccttaa aatttgcata actaattcga gtaaatgcct    1440

| | | | |
|---|---|---|---|
| tttgaagctt | tagttgaata | gttctacaac | tggttgttgc atttgagga ctatcgactt | 1500 |
| gatttgacac | ttgacattgt | ctgatacatg | gcttgtaagt tatgaaaact tttatctagg | 1560 |
| aagaaatccc | aaccagagat | agggagctgt | cacttggtta tgagctactg gctcaaagtt | 1620 |
| caagtttgac | cagttaattt | tagatcttca | ccaggataac atttagagtc taatcaaatt | 1680 |
| ctgaagcagt | attgtgcact | aataagagga | acacatgaag gatgtagcac tactaggtta | 1740 |
| tgttacctta | tttactaatg | attgacaacc | agcttaaatg atgacaaata gtcttatatt | 1800 |
| tgctttttca | cattgctcat | gacttgggat | atttccgaat caacatattt tagttcttta | 1860 |
| tgtacttaac | tacttatcaa | aaattatcc | ctgctagatg ttagtgttca agcaaccatg | 1920 |
| ctagctttta | aggaagctcc | ttctttgatt | catgccatct ttccgaaatc gatgccttac | 1980 |
| gttactgtca | ttttctaat | tttcatttca | gtggattgag gagccgtcac ttttgattac | 2040 |
| acgatttgag | tatgcaaacc | ttttccacac | agttaccgat tggtatagtg catacgtggc | 2100 |
| atccagggtt | actggcttgc | ccagtcggcc | acatttggtt tttgtagatg gccattgtga | 2160 |
| g | | | | 2161 |

<210> SEQ ID NO 19
<211> LENGTH: 2145
<212> TYPE: DNA
<213> ORGANISM: Artificial sequence
<220> FEATURE:
<223> OTHER INFORMATION: Sequence of the PCR produced fragment

<400> SEQUENCE: 19

| | | | | |
|---|---|---|---|---|
| atgaacaaga | aaaagctgaa | atttcttgtt | tctctcttcg ctctcaactc aatcactctc | 60 |
| tatctctact | tctcttccca | ctctgatcac | ttccgtcaca aatcccccca aaaccacttt | 120 |
| cctaataccc | aaaaccacta | ttccctgtcg | gaaaaccacc atgataattt ccactcttct | 180 |
| gtcacttccc | aatataccaa | gccttggcca | atttttgccct cctacctccc ctggtctcag | 240 |
| aatcctaatg | tttctttgag | atcgtgcgag | ggttacttcg gtaatgggtt tactctcaaa | 300 |
| gttgatcttc | tcaaaacttc | gccggagctt | caccagaaat tcggcgaaaa caccgtatcc | 360 |
| ggcgacggcg | gatggtttag | gtgttttttc | agtgagactt tgcagagttc gatttgcgag | 420 |
| ggaggtgcta | tacgaatgaa | tccggacgag | attttgatgt ctcgtggagg cgagaaattg | 480 |
| gagtcggtta | ttggtaggag | tgaagatgat | gagctgcccg tgttcaaaaa tggagctttt | 540 |
| cagattaaag | ttactgataa | actgaaaatt | gggaaaaaat tagtggatga aaaaatcttg | 600 |
| aataaatact | taccggaagg | tgcaatttca | aggcacacta tgcgtgaatt aattgactct | 660 |
| attcagttag | ttggcgccga | tgaatttcac | tgttctgagg ttagattttg aaattttgct | 720 |
| tgatctttaa | attaaaggtt | tgaactttgt | gaatgttggc agatatggaa tacaataatg | 780 |
| gattttgttt | gatctgttta | atgaagattg | tctagaacct cattgttata aatatggttt | 840 |
| gtttgcttca | ttaattaaag | agcattcctt | aaaatctcga ctagatgcca gataacacca | 900 |
| gttagttgac | ttttggatta | tggattttttt | ttcatttaat cagataagat agtcattctt | 960 |
| aaatgtttca | ctaaagaatt | tgtcatgatt | tcagtgtata tctttaagtg tatttggaat | 1020 |
| tttggatttg | gatctagtac | tgaatgggta | actgcacttg tactccccag tcatctgggg | 1080 |
| aggagcaaca | gattaaattc | aagggttgaa | aagtaataca gagtcagaaa ttaaccacaa | 1140 |
| gttggaaaat | ggtaaatgta | tgtggtctaa | gatgattact cctataactt tgatgtcta | 1200 |
| acatggagaa | agttagttga | tttatgctct | ttacttttcc ctttattgat tttggttttc | 1260 |

| | |
|---|---|
| aaattctatc aattcctttg tttgattgct actcagattg aaccttagac ggagtagcaa | 1320 |
| tagaaaagtg aagaaaagcc attttttctc ctttcatctc tttatttctg ttttacacac | 1380 |
| agaatatggt agcatctgtc tgaactagtt aattttattc cttaaaattt gcataactaa | 1440 |
| ttcgagtaaa tgccttttga agctttagtt gtacaactgg ttgttgcatt ttgaggacta | 1500 |
| tcgacttgat ttgacagtgt ctgatacatg gcttgtaagt tatgaaaact tatatctagg | 1560 |
| aagaaatccc aaccagagat agggagctgt cgcttggtta tgagctactg gctcaaagtt | 1620 |
| cgagtttgac cagttaattt tagatcttcg gagtctaatc aaattctgaa gcagtattgt | 1680 |
| gcactaataa gaggaacaca tcaaggatgt agcactgcca ggttatgtta ccttatttac | 1740 |
| taatgattga gaaccagctt aaatgatgac aaatggtctt agatttgttt tttacattgc | 1800 |
| tcatgacttt gggatatttc tggatcaaca ttttccagtt cttatgtac ttatcaaaaa | 1860 |
| attatccctg ctagagccta gatgttagtg ttcaagcaac catgctagct tttaaggaag | 1920 |
| ctccttcttt gattcatgcc atctttccgt aatcgatgcc ttacgttact gtcattttc | 1980 |
| taattttcat ttcagtggat tgaggagccg tcacttttga ttacacgatt tgagtatgca | 2040 |
| aaccttttcc acacagttac cgattggtat agtgcatacg tggcatccag ggttactggc | 2100 |
| ttgcccagtc ggccacattt ggttttttgta gatggccatt gtgag | 2145 |

<210> SEQ ID NO 20
<211> LENGTH: 3089
<212> TYPE: DNA
<213> ORGANISM: Artificial sequence
<220> FEATURE:
<223> OTHER INFORMATION: Sequence of the PCR produced fragment

<400> SEQUENCE: 20

| | |
|---|---|
| atggcaacag ttattccaat tcaaaggtta ccaagatttg aaggtgttgg gtcatcatca | 60 |
| cctacaaatg ttccccaaaa gaaatggtcc aattggctac ctctagtagt tgcacttgtg | 120 |
| gttatagttg aaaattgcatt tctgggtcga ctagacatgg ctgaaaaagc caacctagtc | 180 |
| aactcttgga ctgactcatt ttaccagttt acgacgtcgt cttggtcaac ctccaaagtg | 240 |
| gaaattaatg aggctgggtt ggctgtgtta aggagtggtg agattgatcg gaatttggaa | 300 |
| actgggagct gtgaggagtg gttggaaagg gaggattctg tggagtattc tagagatttt | 360 |
| gacaaagatc caattttgt tcatggcggc gaaaaggtga gattgtttct tgtatatgtt | 420 |
| tattcttttt actaataaat ggggtgaata gagcagaatg gatatagagg attcatatag | 480 |
| ttgaacacga atagtttggg aagttctatg cacttaagga tgtaatagtt tttttttttt | 540 |
| tagtgatgag tgaagggcag ccttgacgta accggtaaag ttgttgccat gtgagtcacg | 600 |
| gttttgagcc gtgaaacaa ccttttgcag acatgcaggg taaggcggcg taaaatagac | 660 |
| ccttgtggtc cggctcttct cggaacccta catagccgga gcttagcgca tcgacctgcc | 720 |
| attttgatga tgagtatttt gatgatgagt ataagttcta tgcactaacg atgtaaaata | 780 |
| gatttacacc attaggtcac ttaaaaggta gtagcagcta attctccatg gaaacattaa | 840 |
| ttggtaatcg agcatctctt ttagactatt atatggatt tgttgcaatt tatgtcttgt | 900 |
| tatttattac atcagttagc tgccagagct ccagacatat ggcttggta gatggaatga | 960 |
| taaaaatttg ttgtttcaaa tgatgcttgg gttttcttct cgtttttttt ttgttcttat | 1020 |
| atcatgttta cagtggaata tcttataaag tacagactat tgacaatatt ccaaaacctc | 1080 |
| ttctatatgg gtaaaaatac tcatgaattt tatatactag tagggaataa ggggaggagc | 1140 |
| cttgagtatc ttctttttttt cttacctttt tttccttcat tacattgaat tcttcataga | 1200 |

| | |
|---|---|
| gcacttaagt ggaatgagca gaaatcaatc agtaaaactg ccatttattg cttgagttta | 1260 |
| tcatgactag ttcttgttcc catgttatcc actggtatat aggtgagagc aggtaacagt | 1320 |
| tactcggtta ccatctttct tcttgatttt tttcccttac catatgcaaa aactgatgtt | 1380 |
| ccttcgatcg ttatctagga ttggaagtct tgtgccgtag gatgtaactt tggtgtggat | 1440 |
| tctgataaga agcctgatgc ggcatttggg acaccacaac aggctggcac ggctagcgtg | 1500 |
| cttcggtcaa tggagtctgc tcaatactat cctgagaaca acatcattac cgcacgacgg | 1560 |
| tgggtaagca catctagaaa aagacttaaa acattctcac cacatttggc agcatttgtc | 1620 |
| gacaattgaa ttttcatctt gtgatcattt tttaatgaaa catatctcac ttggaagttt | 1680 |
| ttgcttgcaa ttagtttctg actagacctt ttttctttgg ataagtaagg tagcatatta | 1740 |
| ttagtaagca gtaccaagaa agtacaaaaa ttgatacttc caaagtctac tcaaaacctg | 1800 |
| aatccagcga ctccaagaac tcatttgtac taactacaag atccgtttta tgccagcaaa | 1860 |
| agagatattg taaacatcta tacttcataa ctataatctc ctcatttttcc ccctcaaaat | 1920 |
| atctcatatt tctttcttgc caaaccgtca aaacaataca caagaaata agcttccaga | 1980 |
| tattcttccc tcttttctcc actgtgcttg ccagctgatg agtgcacctt tgaaattttg | 2040 |
| tggcattacc cagtattaca cccaaaatat attttttatc aggataccct ctaaatatta | 2100 |
| aggaataaag accagatact ccaagaaaga ttacgatgca tcgggagatg actaacagat | 2160 |
| tcacatagac aatcctgatt tgaaaccaca actgatcaca gttgggaata aatctgtaag | 2220 |
| taaaccttca ttacaccatc tatcagtcca aagcttgact ttcctaccat tttcaacttt | 2280 |
| ttgttttatg ttgtctttga actgtcccta gaaattagct attggtctcc ccaaagcaac | 2340 |
| ctcataagga ttacttactg gttttggatc ctaatatctc tccatgccat aaattgactt | 2400 |
| aataacagcc ttccatactg catattttcc atcgttacaa aaaaaagcag ttgcatttgc | 2460 |
| tcaaatagcc tttggaaagg gcatctacaa acatgcaatc ataaagccct caacaacaat | 2520 |
| aactacaaca acaacctagt aaaatcccac aagtgggtc tggggagggt agtgtgtacc | 2580 |
| caaaccttac ccctaccctg agggagtaga gaggttgttt ccgatagacc ctcggctcaa | 2640 |
| gaagatgaaa agagacaata tatcagtact atcaacagat catagagata ataacagcaa | 2700 |
| tcataaaggc ctcatagaca caataacctt aggatcatgt tgtggttata atttaatttt | 2760 |
| tagatctcct atagttcttc tctcaatctt tatatctttc tctagggaaa tctctaacca | 2820 |
| actttattat tcttttctcat gtttcagaag gggatatgat attgtaatga caacaagcct | 2880 |
| ctcttcggat gttcctgttg ggtacttctc ttgggcggag tacgatataa tggctccagt | 2940 |
| gcaacctaaa actgagaatg cattagcagc tgcttttatt tctaattgtg gtgctcgcaa | 3000 |
| cttccggttg caggctcttg aagtccttga aagggcaaat atcaagattg attcttttgg | 3060 |
| cagttgtcat cgtaaccggg atggaaatg | 3089 |

<210> SEQ ID NO 21
<211> LENGTH: 5343
<212> TYPE: DNA
<213> ORGANISM: Artificial sequence
<220> FEATURE:
<223> OTHER INFORMATION: Sequence of the PCR produced fragment

<400> SEQUENCE: 21

| | |
|---|---|
| atggcaacag ttattccaat tcaaaggtta ccaagatttg aaggtgttgg gtcatcatca | 60 |
| cctacaaacg ttccccttaa gaaatggtcc aattggctac ctctagtagt tgcacttgtg | 120 |

```
gttatagttg aaattacatt tctgggtcga ctggacatgg ctgaaaaagc caacctggtc      180
aactcttgga ctgactcatt ttaccagttt acgacgtcgt cttggtcaac ctccaaagtg      240
gaaattagtg agactgggtt gggtgtgttg aggagtagtg aggttgatcg gaatttggaa      300
actgggagct gtgaggagtg gttggaaaag gaggattctg tggagtattc tagagatttt      360
gacaaagacc caattttgt tcatggcggc gaaaaggtga tatagttttc ttgtaaatgt       420 ttatttttt tttagagcag aatgaatata gaggattctt atagttgaac ccgaacagtt       480
taggaggcat agttgattgc tctttttttg atgatgcgta ttagttctat acaggggatt      540
cttggagtaa cggtaaagtt gtctccgtag gtcacaggtt cgagccgtgg gttcgagccg      600
tggaatcagc cacgatgctt gcatcagggt aggctgccta cattataacc ccttcgtgca      660
ccggactact gcccctttagt attagttcta ggcactaacg atgcaaaaaa gatttacgcc      720
ataaggtcac ttaaaaggta gtagcagcta attctccata gaaacattaa ttggtgatcg      780
agcatctctt ttagacgata atttgaattt tgttgcaatt tatgtcttgc tatttattac      840
atcagttagc tgccagagct cgtgtgtgtg tgtgtgtgtg tgtgtgtgtt ccagacttgt      900
ggctttggta ggtggaatga taaaaaaatt gttgtttcaa atgatgcttt ggcattttct      960
tctagctttt ttgttctttt atcatgttta cggtcaaaca tcttataagg actattgacc     1020
atattccaaa accgattata tgggtaaaaa tactcatgaa ttttatatac tagtagggaa     1080
taagtggagg agccttgaat atcttctttt ttcttacctt ttttttcctt attacattga     1140
attcttcata gagcacttaa atggaatgag cagaaattaa tcagtaaaac tgccatttat     1200
tgcttaagtt tatcatgagt agttcttgtt cccatgttat ccactggcat gtagtgagag     1260
caggtaacag ttacctggtt accatctttc ttcttgattt ttttttcctt accatatgcg     1320
aaaactgatg ttccttcaat cattatctag gattggaagt cttgtgccgt aggatgtaac     1380
tttggtgtgg attctgaaaa gaagcctgat gcggcatttg ggacaccaca acaggctggc     1440
acggctagcg tgcttcggtc aatggagtca gctcaatact atcctgagaa caacatcgtt     1500
atggcacgac ggtgggtaag cacatcttga aaaagattta aaacattctc acctacattt     1560
ggcacctgaa agataaatagc atttgccaca tttgagtttt catcttgtga tcgtatctta     1620
atcaaacata tctcacttgg aagttttgc ttgctattag tttctgacta ggccttcctt      1680
ttaaggagca tattattagt aagcagtacc aagaaggtac caaaaaagta caaaaattta     1740
gacttccaaa gacaactcaa aacccgaatc tagtgagttg aagaactcat ttgtactaac     1800
tagaggatcg gttttatgcc agcaaaagag atactgtaaa catctattct ttataactga     1860
attatgctcc tttccccct caaaatatct cgtgtttctt tcttgacaaa atctccaaat      1920
aatacacaaa ggaataagct tgcagatctt cttcagtctt ttctccactg tgcttgccag     1980
ctgatgagtc cacctttgaa atttgtggca ttacccagta ttaccccaa aatatatttt      2040 ttatcagtat accctcaaaa tattaaggaa taaagaccag ctactccaag aaagattacg     2100
atgcatcagg agatgactaa cagattcaca gacaatcctg atttggaacc acactgaaca     2160
cggctgagaa taaatctata agtaaacctt cattcacta ttcatcactc caaagcttga      2220 cttttcccatc attttcagct tttagttttta tgtttatctt tgaactgcct ccaaaaatta    2280
gctattggtc tccacaagca acccataagg attacttact ggttttggat tctaatatct     2340
ctccatgcca taaatcggct ttataacagc cttccatact gcatattttc tatcattacg     2400
aaaaaaaagc agttgcattt gctcaaatag cctttggaaa gggcatctac aaatatgcaa     2460
tcataaagcc ctcatagaca ataatcttag gatcatgttt ttttttatga taatggtaac    2520
```

```
atatatatta ataaataaaa cagcactaga gcagtgccaa gccatattta caagaaaaca    2580
gaaaccagct atgacaacct aagattacag tgcacctatc aggtctacta aagattctgc    2640
ctcctctatc cagttttctt tacaccagaa ataaaacaaa agtaaacact tcatcttgat    2700
gttctgtaaa gaattgcttc tgtcttcaaa agttcttaaa tttctctcct tccagactgt    2760
ccaccatatg cacgcaggaa ccaatcgcca ccatttcttc tgtctcacta taccctcatt    2820
gtaattccaa cacttcaaca tatcacaagt gttagctggc atgctccatt taaggcccac    2880
aatattaaga aatagttgcc acagttggtc agtaaaagga caatgaagaa acaaatggct    2940
attagtttct atagctgtac cacataatag gcatttagag catagctgaa aacctcttct    3000
tctcaagttc tcttgggtta dacaagcctt tcttgtaact aaccatgaaa agcataccac    3060
cttgaaaggt gcctttactt tccaaatatt cctccagggc cattgttcta actgttggtt    3120
tgaagcagcg agtagagtat acgcggatct gaccgtaaaa ttcccactcc ttcaatgatt    3180
ccagcatagt ttatcttcag tttctccaag accttggaat tgttccaaga tattaaagaa    3240
atttacaacc ctttctaatt cccaatcatt caaggccttt ctaaaagtaa cattccatcc    3300
ttgctgaccc caggcagtgt ctaaagtgga tgtaggtgat gttgcaatgc tgaaaaattt    3360
ttgaaaaaat tctttgagag gaccatgtcc taaccagtta tcactccaga aaagtgtttt    3420
ccttccatta ccaacccttta tggttgtatt atcagccaga gtattccagt gaagtctgat    3480
tgacttccat accccaaccc catgtgaact attaacagag ttagagcacc atagtccatt    3540
ttgtccatac ttgtcacaga tgaccttcct ccacaaagca ttagcctttc agattgtacc    3600
tccaaagcca cttcaagagt aaactctgat tgtgggcttt aaggttccta atgcccaaac    3660
cccctttgtc tttgcttgtg ataagggaat tccagttaac taaatgaata gcttccttct    3720
ctctgtttcc ttgccatata aagctccttc ttagtgcatc aattctttc ctcaccttgc    3780 ttggtaaggg aaacaaagac attacacatg taggaagtgc atccaagaca ctattaacca    3840
ataccaccct tccacccaag gataaatact ggctcttcca ggttgatagc ctttttttcac    3900 atctttcaag aaccccattc catatttctt gagctttgtt cttggagcct agagataaat    3960
ccaaatatat agttggtaga gaacccacct catatcccag tatagctgct agggcctgga    4020
tatcatccac ttctttaact gggaacaaca tgctcttcct ccgatttaca tggagccctg    4080
agactgcttc aaatataaca agaatgactc ttagatattt tagttgatct gcctttgcct    4140
cacaaaaaac taaagagtca tcagcatata gaagatgggt gatctccaca ctatctccct    4200
ccctgtttga agctttaaaa cctttcagcc aaccattgtt gtttgcattt tttaacattt    4260
ggttcaatcc ttccatagca aagaggaaaa gaaaggtga taagggatcc ccttgtctca    4320
aacctctctc agaaggaaaa aatccctctg gagaaccatt caccaaaatg gaaaatctga    4380
ctgttctgat gcagaaagat atccagttga tccacttcct accaaaaccc atatcctgaa    4440
gaactttgag taaaaagttc caattaacat gatcataggc cttctcaata tcaagcttac    4500
agagaattcc gggaacctgc cctttaagt caggaatcca cacattcatt tgcaatcaag    4560
gaagcatcca tgatttgcct gcctcttatg aaggccattt gatgcccatt cactagtttg    4620
tccaccactt tcttgagcct ctctgtcaat agtttggaaa tgatcttgta aatgcttcct    4680
gtaagactaa ttggtctgaa gtccttgagt tccttagcac cattcttttt tggaataagg    4740
gctatgtaag tagcattgaa actcttctca aaatattcat tgttgtggaa gtttctgatg    4800
gtatgcatga tgtcttcttt cacaatctcc cagcaattat ggaaaaaccc catagagaaa    4860
```

```
ccatcagggc cggtgctttt gtcagctgca catatcttca aggtctcaaa cacttcttgt    4920
tcttcaaatt ctccttgtag caattcatta tcttcctata gttctcctat agttctaatt    4980
gtctctcaat ctttatatct ttaaatttaa attttagatc tcctatagtt cttctctcaa    5040
tctttatatc tttctctagg gaaatctcta accaactttta ttattctttc tcatgtttca   5100 gaagggata tgatattgta atgacaacaa gcctctcttc ggatgttcct gttgggtact     5160
tctcttgggc ggagtatgat ataatggctc cagtgcaacc taaaactgag aatgcgttag    5220
cagctgcttt tatttctaat tgtggtgctc gcaacttccg gttacaggct cttgaagtcc    5280
ttgaaagggc aaatatcaag attgattctt tggcagttg tcatcgtaac cgggatggaa     5340
atg                                                                  5343
```

<210> SEQ ID NO 22
<211> LENGTH: 834
<212> TYPE: DNA
<213> ORGANISM: Artificial sequence
<220> FEATURE:
<223> OTHER INFORMATION: Sequence of the PCR produced fragment

<400> SEQUENCE: 22

```
ggttagtgct cttcgttaca ttgagtcaca cgattaattt atgaagccaa agttcttaag     60
gaccatggcg tggttgagat ttaaactttg cataagcttg ctaaccaatt ttattttttt    120
cactcacata ccagaagggg atatgatgtt gtaatgacaa caagcttctc ttcagatgtt    180
cctgttggat acttctcttg ggctgagtat gatatcatgg ctccagtaca acctaaaaca    240
gagaatgtct tagcagccgc tttcatttct aattgtggtg ctcgcaattt ccgcttgcaa    300
gctttagaag cccttgaaag ggcaaatatc agaattgatt cttatggcag ttgtcatcat    360
aacagggatg gaagaggtta gtatatttca attatccaaa cttactgaag gattagagga    420
tagaatacgg atggtgcaat tttaagcagt gtcactaggg agctaattct tgtccataga    480
gtagtattat gggtttgatt gactcttcct cgggtatcac accttcctcc agaagacagg    540 atttttactac cagtgcaaac cttttttttc tctcctggct aatgtgagca cgcatgtcgt    600
cgttttttta gtgatttgaa tttatgctag tccaatgatt gcttgtcaat ggattatttt     660 gctcttttc ttgtttaaaa tttgagtttc aattttgcca cctgataaga ataaagttgg      720
aatacaacat tcatttaaat agttcgattt cattctgagg aagttaggct gagatttgtt     780
ggaaagagac gtatagcgag aaaaaatgtt gtggacaaat catctttctg gatg           834
```

<210> SEQ ID NO 23
<211> LENGTH: 832
<212> TYPE: DNA
<213> ORGANISM: Artificial sequence
<220> FEATURE:
<223> OTHER INFORMATION: Sequence of the PCR produced fragment

<400> SEQUENCE: 23

```
ggttagtgct cttcgttaca ttgagtcaca agattaattt atgaagccaa agttcttaag     60
gaccatggcg tggttgagat ttaaactttg cataagcttg ctaacctatt ttattttttc    120
cactcacata ccagaagggg atatgatgtt gtaatgacaa caagcctctc ttcagatgtt    180
cctgttggat atttctcttg ggctgagtat gatatcatgg ctccagtaca acctaaaaca    240
gagaatgcct tagcagccgc tttcatttct aattgtggtg ctcgcaactt ccgcttgcaa    300
gctttagaag cccttgaaag ggcaaatatc agaattgatt cttatggcag ttgtcatcat    360
aacagggatg gaagaggtta gtatatctca attatccaaa cttactgaag gattagagga    420
```
tagaatatgg atggtgcatt tttaagcagt gccactaggg agctaattct tgtccataga    480
gtagtattat ggatttgatt gactcttcct cgggtgtcac accttcctcc agaagacagg    540
attctactac cagtgcaaac cttatttttt ttctcctggc taacgtgagc atgcatgtcg    600 ttttttagt gattcgaatt tatgctagtc cgatgattgc ttgtcaatgg attattttgc    660 tcttttctt gtttaaaatt tgagtttcaa ttatgccacc tgataagaat aaagttggaa    720
tacaacattc atttaagtag ttcgatttca ttctgaggaa gtcaggctga aatttgttgg    780
aaagagacgt atagtgagaa aaatgttgt ggacaaatca tctttctgga tg    832

<210> SEQ ID NO 24
<211> LENGTH: 23
<212> TYPE: DNA
<213> ORGANISM: Artificial sequence
<220> FEATURE:
<223> OTHER INFORMATION: DNA sequences selected as the CAS9 targets
      (crRNAs)

<400> SEQUENCE: 24
gagaaattgg agtcggttat tgg    23

<210> SEQ ID NO 25
<211> LENGTH: 21
<212> TYPE: DNA
<213> ORGANISM: Artificial sequence
<220> FEATURE:
<223> OTHER INFORMATION: DNA sequences selected as the CAS9 targets
      (crRNAs)

<400> SEQUENCE: 25
gatcggaatt tggaaactgg g    21

<210> SEQ ID NO 26
<211> LENGTH: 24
<212> TYPE: DNA
<213> ORGANISM: Artificial sequence
<220> FEATURE:
<223> OTHER INFORMATION: DNA sequences selected as the CAS9 targets
      (crRNAs)

<400> SEQUENCE: 26
gctggcacgg ctagcgtgct tcgg    24

<210> SEQ ID NO 27
<211> LENGTH: 23
<212> TYPE: DNA
<213> ORGANISM: Artificial sequence
<220> FEATURE:
<223> OTHER INFORMATION: DNA sequences selected as the CAS9 targets
      (crRNAs)

<400> SEQUENCE: 27
gccgctttca tttctaattg tgg    23

<210> SEQ ID NO 28
<211> LENGTH: 23
<212> TYPE: DNA
<213> ORGANISM: Artificial sequence

```
<220> FEATURE:
<223> OTHER INFORMATION: DNA sequences selected as the CAS9 targets
      (crRNAs)

<400> SEQUENCE: 28
gggcttctaa agcttgcaag agg                                                  23
```